United States Patent [19]
Bailey

[11] Patent Number: 5,797,743
[45] Date of Patent: Aug. 25, 1998

[54] AUTOCLAVABLE DENTAL HANDPIECE WITH DISPOSABLE HIGH SPEED TURBINE

[75] Inventor: Ronald L. Bailey, Harvester, Mo.

[73] Assignee: Young Dental Manufacturing Company, Inc., Earth City, Mo.

[21] Appl. No.: 639,401

[22] Filed: Apr. 29, 1996

[51] Int. Cl.[6] ..................................................... A61C 1/10
[52] U.S. Cl. ........................................... 433/126; 433/132
[58] Field of Search ................................. 433/126, 132, 433/82

[56] References Cited

U.S. PATENT DOCUMENTS

| | | |
|---|---|---|
| Re. 31,965 | 8/1985 | Kerfoot, Jr. . |
| 3,815,241 | 6/1974 | Lingenhohle et al. ............... 433/82 |
| 3,955,284 | 5/1976 | Balson . |
| 4,217,101 | 8/1980 | Loge ................................ 433/126 |
| 4,219,330 | 8/1980 | Jaremus . |
| 4,231,739 | 11/1980 | Iudica . |
| 4,406,470 | 9/1983 | Kataoka et al. . |
| 4,533,324 | 8/1985 | Nakanishi . |
| 4,795,343 | 1/1989 | Choisser . |
| 4,842,516 | 6/1989 | Choisser . |
| 4,869,779 | 9/1989 | Acheson . |
| 4,921,424 | 5/1990 | Kimura . |
| 4,941,828 | 7/1990 | Kimura ............................. 433/126 |
| 4,966,552 | 10/1990 | Gonser . |
| 5,088,924 | 2/1992 | Woodward ......................... 433/126 |
| 5,156,547 | 10/1992 | Bailey .............................. 433/126 |
| 5,252,065 | 10/1993 | Nakanishi ......................... 433/126 |
| 5,252,067 | 10/1993 | Kakimoto ......................... 433/126 |
| 5,308,242 | 5/1994 | McLaughlin et al. . |
| 5,334,013 | 8/1994 | Meller ............................. 433/132 |
| 5,336,089 | 8/1994 | Sakurai . |
| 5,340,311 | 8/1994 | Sakurai . |
| 5,340,312 | 8/1994 | Murase ............................ 433/132 |
| 5,342,196 | 8/1994 | Van Hale . |
| 5,374,189 | 12/1994 | Mendoza . |
| 5,476,380 | 12/1995 | Rosenstatter ..................... 433/132 |
| 5,507,642 | 4/1996 | Wohlgemuth ..................... 433/132 |
| 5,538,425 | 7/1996 | Reeves et al. ..................... 433/82 |
| 5,554,026 | 9/1996 | Van Hale ......................... 433/132 |

*Primary Examiner*—Paul J. Hirsch
*Attorney, Agent, or Firm*—Polster, Lieder, Woodruff & Lucchesi

[57] ABSTRACT

A high-speed dental handpiece of the present invention includes a metal non-disposable body and a plastic disposable cartridge received in the body. The body is a one piece body and has a sleeve and an annular head at an end of the sleeve. The sleeve carries an air input line, an air exhaust path, a water line and a fiber optic cable. The air input and water lines are operatively connected to a supply of air and water, respectively. The fiber optic cable is operatively connected to a source of light to carry the light to a patient's mouth to enable a dentist to more clearly see the area being operated upon. The disposable cartridge carries a turbine and is placed in communication with the air input lines to drive the turbine. A bit is received by the turbine and the water is directed toward the bit for cooling. The cartridge is at least partially made of light transmitting material and the fiber optic cable abuts the cartridge to transmit light therethrough. The fiber optic cable may be removably inserted in the handpiece. The use of a disposable cartridge allows for thorough cleaning and sterilizing of the handpiece body without worry of damaging a turbine or its related bearings.

83 Claims, 7 Drawing Sheets

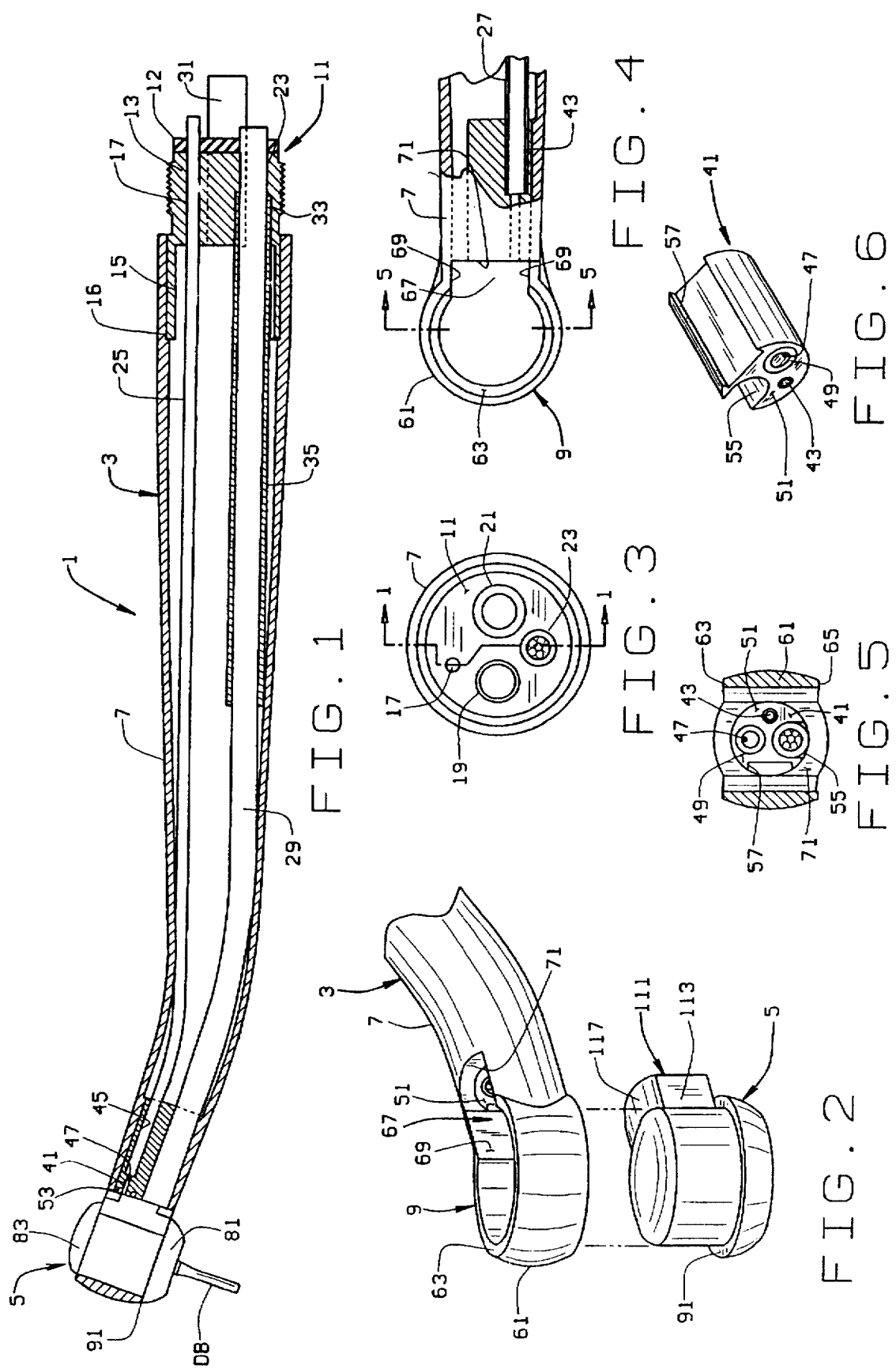

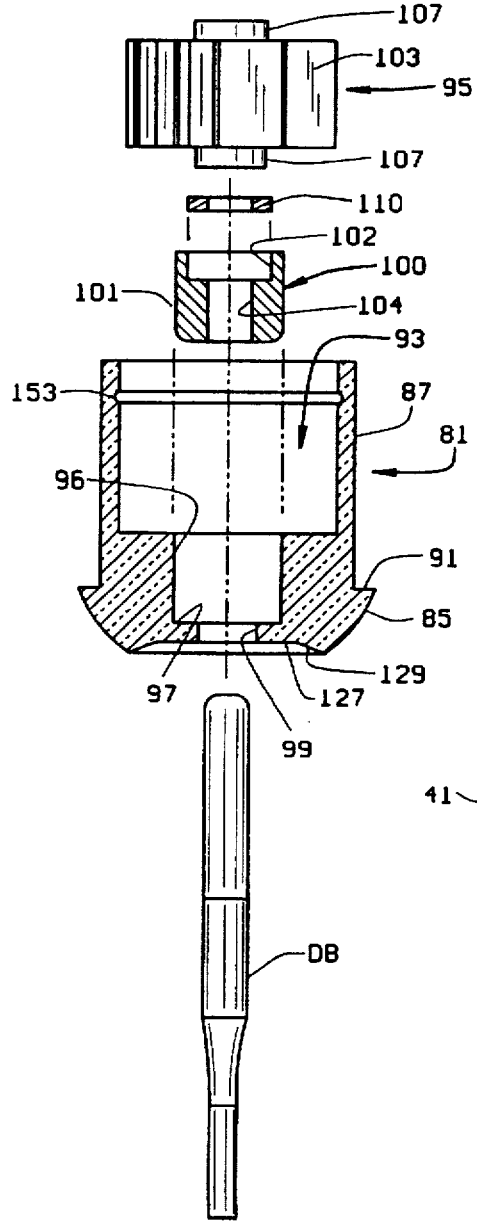
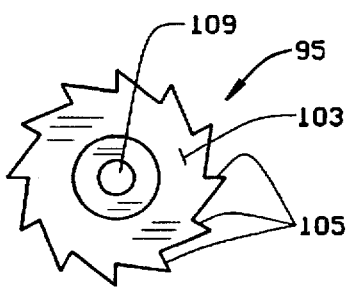
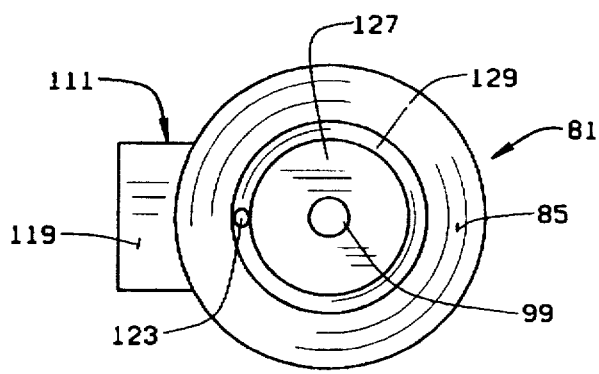
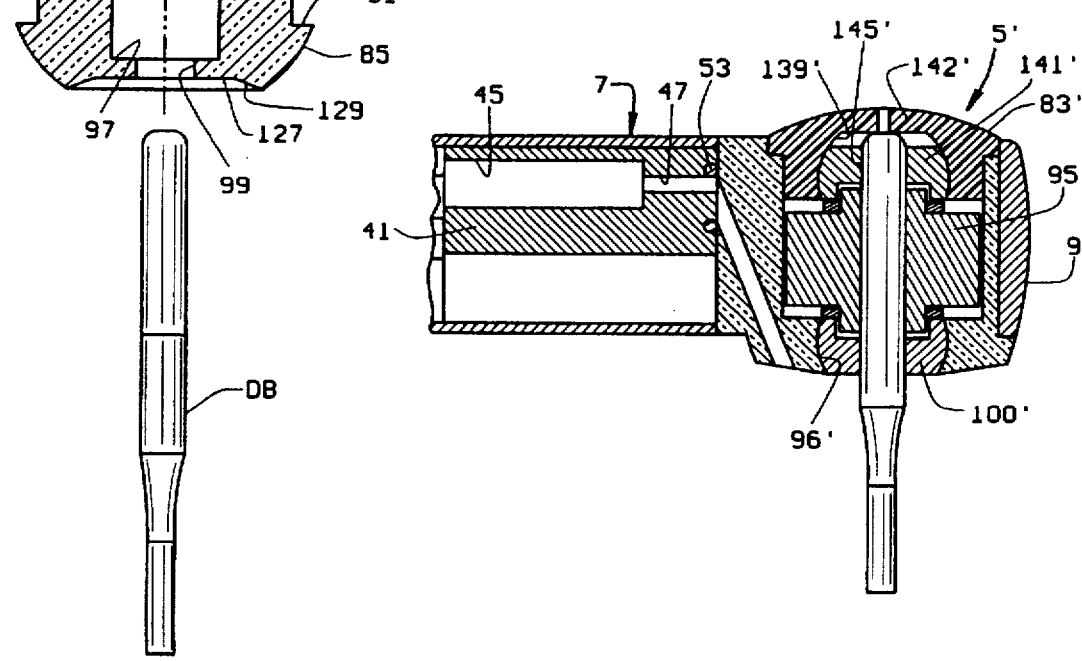
FIG. 11
FIG. 12
FIG. 13
FIG. 14

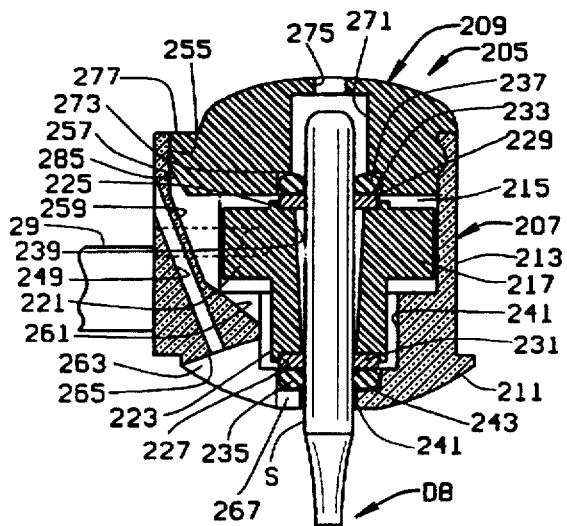
FIG. 15
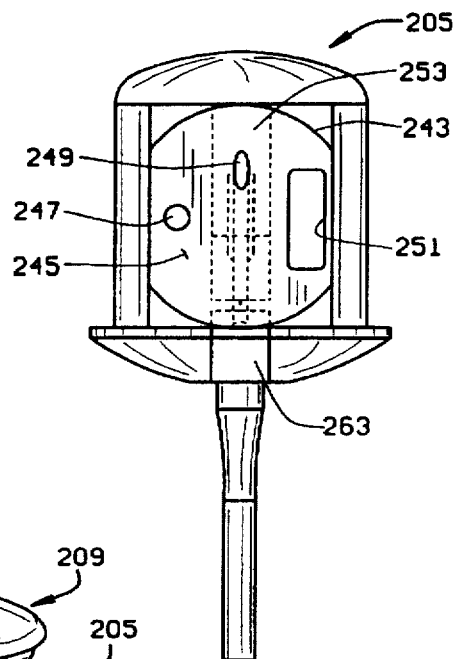
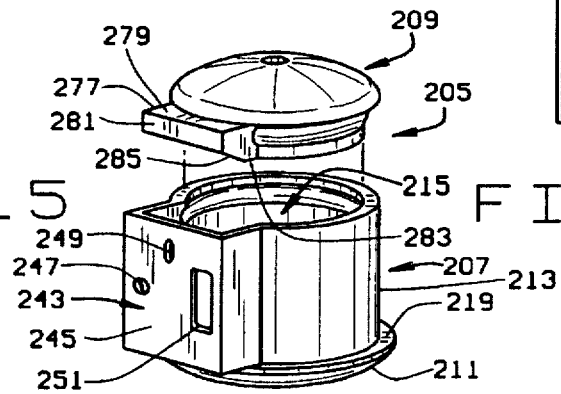
FIG. 16
FIG. 17
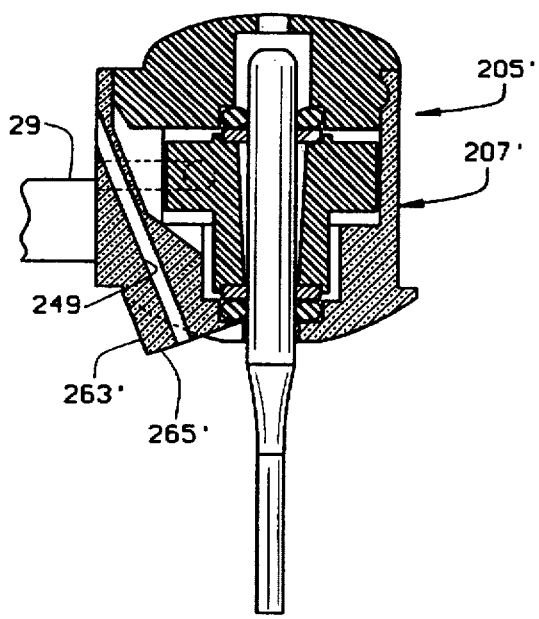
FIG. 18
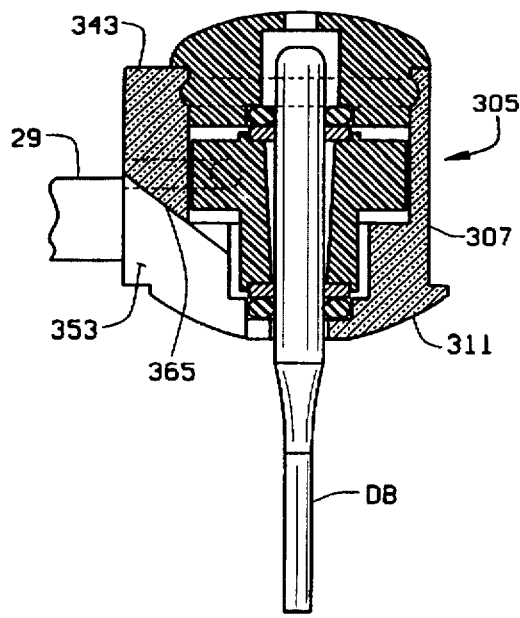
FIG. 19

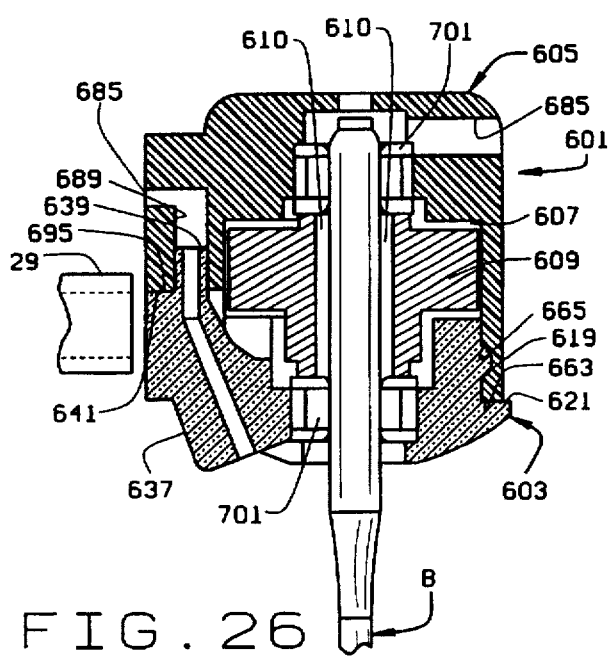
FIG. 26
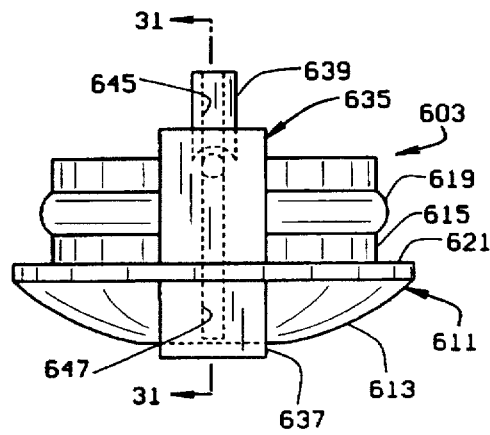
FIG. 27
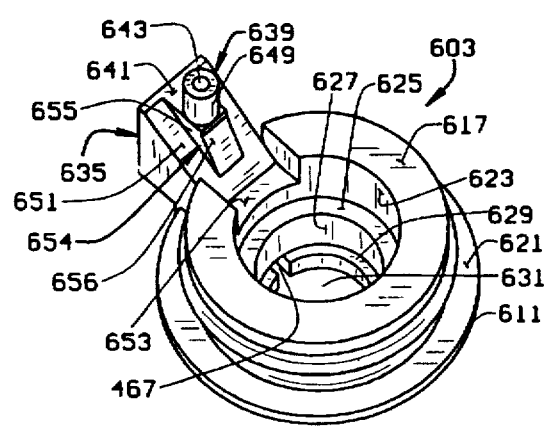
FIG. 29
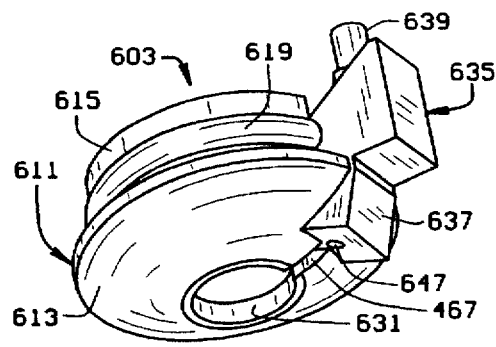
FIG. 28
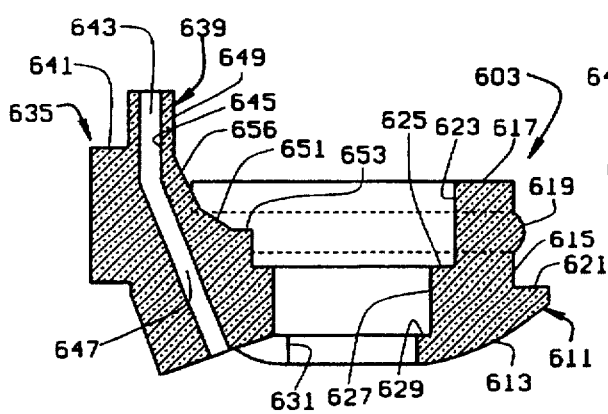
FIG. 31
FIG. 30

AUTOCLAVABLE DENTAL HANDPIECE WITH DISPOSABLE HIGH SPEED TURBINE

BACKGROUND OF THE APPLICATION

This invention relates to dental handpieces, and in particular to air-driven high speed turbines.

Dentists use high speed turbines in dental handpieces to rotate dental burrs at high speeds (i.e. in excess of 100,000 rpm). To enable the drill to be rotated at such high speeds, the drill bit is held by bearings and a turbine in the head of the handpiece. Air is forced into the head of the handpiece to rotate the turbine, which in turn rotates the drill bit. The air is then exhausted out the back of the handpiece.

When the handpiece is used, the head of the handpiece, which is inserted in the patient's mouth, becomes contaminated. The handpiece must thus be cleaned and sterilized between uses. The most effective way to fully sterilize the hand piece is to autoclave it. However, the heat from the autoclave can, over time, damage the turbine bearings. Once the bearings have been damaged, the high speed handpiece cannot be effectively run at the necessary speeds to be used as a drill. Further, grit can sometimes get into the handpiece. This grit can sometimes be removed by ultrasonically cleaning the handpiece. However, ultrasonic cleaning will also damage the bearings. Proper cleaning and sterilizing of the handpiece will thus effectively shorten the life of the high speed handpiece. High speed handpieces are very expensive. Thus, to prevent the possibility of shortening the useful life of the handpiece, some dentists resort to merely wiping down the outside of the handpiece. This may clean off the contaminants on the outside of the handpiece, but it cannot not properly disinfect the exterior of the handpiece, and does not clean or disinfect the interior of the handpiece. Grit which may accumulate in the handpiece will therefore remain in the handpiece unless the handpiece is opened and manually cleaned.

To overcome this problem, some manufacturers have introduced fully disposable high speed handpieces. One such handpiece was produced by OralSafe, of Temecula, Calif. Another is shown in U.S. Pat. No. 4,842,516, to Choisser. Although fully disposable handpieces overcome the problems associated with the inability to fully clean a high speed handpiece without ruining its bearings, they are still expensive.

Currently available high speed handpieces typically include a fiber-optic cable to light the area where the doctor is working in the patient's mouth and a water stream to cool the bit as the dentist performs a drilling operation on the patient's teeth. Typically, the water and light outputs are located on the sleeve of the handpiece, behind the head which carries the turbine. The placement of the light and water outputs can be seen, for example, in U.S. Pat. No. 4,966,552 to Gonser. The light coming from an area behind the head of the handpiece does not adequately light the work area in the patient's mouth. Because the light is rather far from the drill bit, the light becomes diffused because of the longer distance traveled, and thus does a poorer job of lighting the workarea. Further, because the light comes from one direction, rather than all around the drill, it is possible that the light will be totally ineffective for use when the handpiece is used in certain angles. Similarly, with the water exiting the handpiece from the sleeve, the water is not accurately aimed at the drill bit, or may not contact the drill bit. Thus, the drill bit may not be adequately cooled during use.

SUMMARY OF THE INVENTION

One object of the present invention is to provide a high-speed dental handpiece which may be autoclaved and/or ultrasonically cleaned.

Another object is to provide such a handpiece which has a metal, autoclavable body part and a disposable cartridge which carries the turbine and bearings.

Another object is to provide such a handpiece in which the cartridge may be inexpensively produced.

Another object is to provide such a handpiece in which the cartridge can be run at high speeds for at least the duration of one session.

Another object is to provide such a handpiece which will more fully light the area in which the dentist is working.

Another object is to provide such a handpiece in which the cooling water will be more accurately directed at the drill bit so that more of the cooling water will contact and cool the drill bit.

Another object is to provide such a handpiece having a removable fiber-optic bundle.

These and other objects will become apparent to those skilled in the art in light of the following disclosure and accompanying drawings.

In accordance with the invention, generally stated, a high-speed dental handpiece of the present invention includes a metal non-disposable body and a disposable cartridge received in the body. The body is a one-piece body having a sleeve and an annular head at an end of the sleeve. The sleeve carries an air input line, a water line and a fiber optic cable and defines an exhaust air path. The air input and water lines are operatively connected to a supply of air and water, respectively. The fiber optic cable is operatively connected to a source of light to carry the light to the disposable cartridge and transmit the light through the cartridge to light up the area in the patient's mouth where the doctor or dentist is working so that the doctor or dentist to more clearly see the area being operated upon.

The disposable cartridge is received in the head of the body. The disposable cartridge includes a cartridge body which receives a turbine and a cap which closes the cartridge body. The cartridge body has a bottom portion and an annular wall extending upwardly from the bottom portion to define an upwardly opening chamber or cavity in which the turbine is received. The cartridge body bottom portion has a centrally positioned bore through which a bit is passed to be removably received in the turbine. The cartridge body wall is sized so that it is frictionally received in the annular head of the handpiece. The cartridge body wall and bottom portion define an outwardly radially extending shoulder which abuts a bottom surface of the annular head.

The cartridge cap includes an upper portion and a cylindrical lower portion. The upper portion and lower portions define a shoulder which abuts the annular wall of the cartridge body. The cylindrical lower portion is sized to be frictionally received within the cartridge body. The cartridge cap can be glued or snap-locked to the cartridge body to prevent the cartridge from opening during use.

The cartridge body bottom portion and the cap define bores which receive self-lubricating bearings. The turbine includes upper and lower bosses which are received in the bearings. Washers may be positioned between the turbine bosses and the bearings to vertically position the turbine in the cartridge to substantially prevent axial movement of the turbine relative to the cartridge. The bearings have bores aligned with the turbine bore and the dental bit has a shaft extending through the bores. In one embodiment, the bearings are self-aligning. In this embodiment, the cartridge body bore and the cap bore are defined by curved surfaces and the bearings have arcuate outer surfaces. The bearings, in this second embodiment, may pivot independently of each other about a vertical axis in the bores such that the bearing bores may be aligned with the turbine bore.

To facilitate positioning of the cartridge in the handpiece body, the body sleeve has a rectangular cutout defined by side walls and a back edge and which opens into the annular head. A manifold is positioned in the forward end of the sleeve and forms a back wall of the cutout. The air input and water lines in the sleeve are received in the manifold to place them in fluid communication with the cutout. The manifold includes an opening to allow for exhaust air to enter the sleeve exhaust path. The cartridge includes a heel which is received in the rectangular cutout. The cartridge heel has an air supply bore and an air exhaust bore extending from the back wall of the heel to the cartridge chamber. The air supply bore and the air exhaust bore are in communication with the air supply line and air exhaust line, respectively, such that air may be introduced into and exhausted from the cartridge chamber. The fiber optic cable extends through the manifold and ends at the forward wall of the manifold to abut the back wall of the cartridge body heel. The heel serves as a key to properly align the various bores of the manifold with the openings in the cartridge. The cartridge body is made of a light transmitting (preferably clear) plastic so that the light from the fiber optic cable may be transmitted though the cartridge body to illuminate patient's mouth. In a first embodiment, the heel of the cartridge is substantially solid, and the light is transmitted through the heel. In a second embodiment, the heel defines a hollow upper portion which has a diagonal wall. The wall acts as a mirror to reflect the light from the fiber optic cable and aims the light through the bottom portion of the heel to the work area. In a third embodiment, the heel defines a lower hollow slot having a diagonal upper wall. This upper wall acts as mirror and reflects the light off the surface, through the slot, and to the work area. In this embodiment, a part of the light transmitted from the cartridge does not pass through any transparent material and only passes through air. In both the second and third embodiments, a portion of the light is aimed to the workarea to effectively provide a spot light on the workarea. The remaining light which passes through the cartridge will provide a bit of background lighting to light a wider area of the workarea than is accomplished in the prior art.

Because the turbine is disposable, the only part of the handpiece that need be cleaned is the body. Because the body contains no parts which are affected by an autoclave or ultrasonic cleaner, the body can be safely cleaned and sterilized without fear of reducing the operating life of the handpiece. The fiber optic cable may be removably received in the sleeve. Thus, by removing the fiber optic cable, which is virtually the only part that may be damaged after multiple autoclavings and ultrasonic cleaning procedures, all parts of the handpiece body are fully autoclavable and ultrasonically cleanable.

BRIEF DESCRIPTION OF THE DRAWINGS

FIG. 1 is a is a cross-sectional view of a handpiece of the present invention, taken along line 1—1 of FIG. 3;

FIG. 2 is an exploded view of a body of the handpiece and an associated disposable cartridge, which when assembled together form a complete handpiece;

FIG. 3 is a rear elevational view of the handpiece;

FIG. 4 is a top plan view, partially cut away, of a forward portion of the handpiece body;

FIG. 5 is a view taken along line 5—5 of FIG. 4;

FIG. 6 is a perspective view of a manifold of the handpiece body;

FIG. 11 is an exploded cross-sectional view of the cartridge;

FIG. 12 is a top plan view of a turbine used in the cartridge;

FIG. 13 is a bottom plan view of the cartridge;

FIG. 14 is an enlarged cross-sectional view of a second embodiment of the cartridge placed in the head of the handpiece body;

FIG. 15 is a cross-sectional view of a third embodiment of the cartridge;

FIG. 16 is an exploded perspective view of the cartridge of FIG. 15, with the internal components excluded for clarity;

FIG. 17 is a rear elevational view of the cartridge of FIG. 15;

FIG. 18 is a cross-sectional view of a variation of the cartridge of FIG. 15;

FIG. 19 is a cross-sectional view of a fourth embodiment of the cartridge;

FIG. 26 is a cross-sectional view of a fifth embodiment of the disposable cartridge of the present invention;

FIG. 27 is a rear elevational view of a lower portion of the cartridge of FIG. 26;

FIG. 28 is a bottom perspective view of the lower portion of the cartridge;

FIG. 29 is a top perspective view of the lower portion of the cartridge;

FIG. 30 is a top plan view of the lower portion;

FIG. 31 is a cross-sectional view of the lower portion taken along line 31—31 of FIG. 27;

DESCRIPTION OF THE PREFERRED EMBODIMENT

Figures 7, 8:
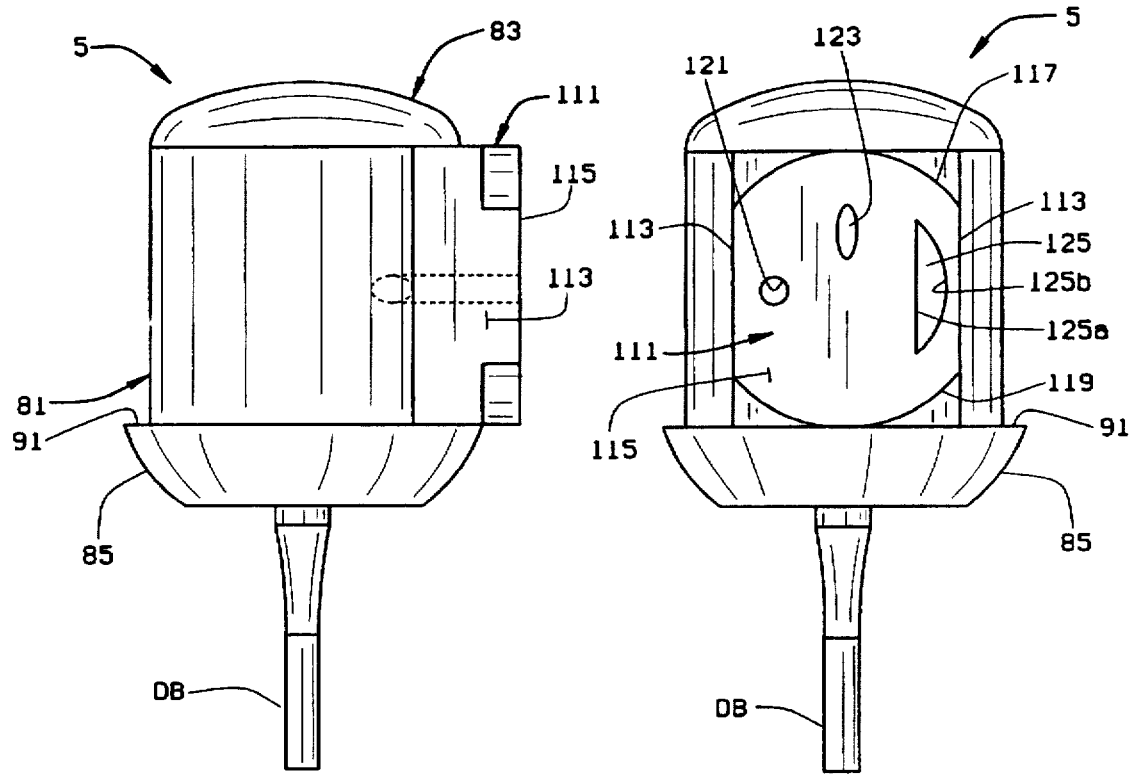
FIG. 7 is a side elevational view of a disposable cartridge used with the handpiece body.
FIG. 8 is a rear elevational view of the cartridge.

A high-speed handpiece 1 is shown generally in FIG. 1. The handpiece 1 includes a handpiece body 3 which removably receives a disposable cartridge 5. The handpiece body 3 includes a hollow sleeve 7 and a head 9. A connector 11 is received in the back of the handpiece 7. The connector 11 connects the handpiece to conduits which carries air and water, a source of light, and an exhaust line. A rubber gasket 12 is provided to make fluid tight connections between the connector 11 and the conduits. The body 3, connector 11, and conduits are preferably made of a material, such as metal, which can withstand multiple autoclavings.

Connector 11 includes a connector body 13 having a forwardly extending cylindrical wall 15. The wall 15 is sized to be force fit into the back of the sleeve 7. The forward edge of the wall 15 abuts a shoulder 16 in the sleeve to prevent the connector 11 from being inserted too far into the sleeve. The connector body 13 has external threads to connect the handpiece 1 to sources of air, light, and water, as is well known in the art. Although the connection to the conduit which carries the air, water, light, and exhaust is shown to be a screw-type connection, other types of connections can be used. The connector body has four bores 17, 19, 21, and 23 (FIG. 3) extending therethrough for water input, air input, air exhaust, and fiber optic cables, respectively. A water tube 25 (FIG. 1), an air supply tube 27 (FIG. 4), and a fiber optic cable 29 (FIG. 1) pass through connector body bores 17, 19, and 23, respectively, and extend to the end of sleeve 7, as will be discussed below. A stub tube 31 extends through connector bore 21 to provide an exhaust port to carry exhaust air away from the handpiece 1. Tubes 25, 27, and 31 are preferably metal tubes. No internal tube is provided for the exhaust air, and the hollow sleeve 7 itself defines an exhaust tube which delivers exhaust air to stub tube 31.

The opening 23 through which the optic fiber bundle 29 extends is counterbored as at 33. The counterbore 33 receives a guide tube 35 which extends partially through the sleeve 7, preferably about half-way through the sleeve. The fiber optic cable 29 is threaded or passed through the guide tube 35 to guide the cable 29 through the handpiece to the end of the sleeve 7. The fit of the fiber optic cable 29 in the guide tube 35 and connector 11 is sufficiently tight to hold the cable 29 in place in the sleeve 7, but yet not so tight that the cable may be easily removed for replacement if necessary.

A generally cylindrically shaped manifold 41 (FIGS. 5, 6, and 14) is force fit in the sleeve 7 near its forward end. The manifold 41 includes two bores 43 (FIG. 6) and 45 (FIG. 14) for the air input and water input, respectively. As seen in FIG. 1, water tube 25 is received in bore 45. The bore 45 (as best seen in FIG. 14) is stepped down to define a smaller diameter bore 47 which opens into body head 9. A groove 49 (FIG. 5) is formed in the front surface 51 of the manifold 41 to receive an O-ring 53 (FIGS. 1 and 14). The groove 49 is not formed concentrically with bore 47. Rather, the bore 47 opens into the circle defined by the groove 49 adjacent the groove, as is best shown in FIG. 5. The manifold 41 has a pair of longitudinal or axial cut-outs 55 and 57 formed in the outer surface of the manifold. Cut-out 55 is shaped generally like an arch and is sized so that the fiber optic cable 29 may be easily slid into the arch. As seen in FIG. 1, the cable 29 passes though the manifold arch 55 until its forward end is flush with the front surface 51 of the manifold and in abutting relationship with the back of cartridge 5. The second cut-out 57 is generally rectangular in shape and opens from the body head into the sleeve 7 to allow for exhaust air to pass from the cartridge 5 into the body 3, as will be described below.

The connector 11 and manifold 41 are made of a material which can withstand autoclaving and ultrasonic cleaning.

The water tube 25, input air tube 27, and exhaust tube 31 are preferably metallic and can withstand both autoclaving and ultrasonic cleaning. The hollow sleeve 7 serves to carry the exhaust from the body head to the tube 31. Thus there is no need to provide for an exhaust tube extending through the body. However, such a tube could be provided if desired.

As best seen in FIGS. 2 and 4, the body head 9 is defined by an annular ring or wall 61 which extends forwardly of sleeve 7. It will be appreciated that "annular" is used in a broad sense to mean that the wall 61 is generally ring-like in shape. The wall 61 has a generally planar top surface 63 and a generally planar bottom surface 65 (FIG. 5). As seen in FIGS. 1 and 5, the outer surface of wall 61 is preferably slightly convex in vertical cross-section. A rectangular opening 67 (FIG. 4) is formed at the forward end of the sleeve 7 and opens into the head 9. Opening 67 extends vertically through the sleeve 7 is defined by two generally vertical side walls 69, a front surface or edge 71 of sleeve 7, and the front surface 51 of manifold 41. The manifold 41 is received in sleeve 7 such that the forward surface 51 of manifold 41 is flush with the front surface 71 to provide an even or planar surface, as is shown in FIGS. 2 and 5.

To assemble the body 3 of the handpiece 1, the air supply tube 27 and the water supply tube 25 are force fit in their respective bores in the manifold 41. The manifold 41 is then inserted into the handpiece such that the front surface 51 of the manifold is flush with the surface 71 at the front of the sleeve 7. As seen in FIG. 1, the sleeve tapers such that the inner diameter of the sleeve narrows from the back to the front. The manifold 41 with the tubes 25 and 27 can thus easily be inserted in the sleeve from the back of the sleeve. To facilitate inserting the manifold 41 into the sleeve, the sleeve is preferably straight when the body is assembled and then bent to the configuration shown in FIG. 1 after the body has been assembled. The tubes 25 and 27 can be cut to length before or after they are inserted in the manifold 41. Once the manifold 41 and tubes 25 and 27 are inserted in the sleeve, the connector 11 is inserted into the sleeve 7. Prior to inserting the connector 11 into the sleeve, the guide tube 35 for the fiber optic cable 29 is inserted in the counter bore 33 in the connector. The stub tube 31 may be force fit in its bore in the connector at any time. Once the manifold 41 and connector 11 have been placed in the sleeve, the fiber optic cable 29 can be inserted into the sleeve. The cable 29 is simply threaded or passed through connector bore 23 and guide tube 35. The guide tube 35 serves to direct the fiber optic cable 29 to the arched cut-out 55 in the manifold 41. The cable 29 is passed through the sleeve 7 until its front end is flush with the front surface 51 of the manifold 41. The cable is of a length that its back end is flush with the back of the connector 11 when its front end is preferably flush with the manifold surface 51.

The configuration or spatial relationship of the tubes at the back of the connector are fairly standard so that the handpiece can be connected to a standard control unit, as is known in the art. The manifold 41 and connector 11 are positioned in the sleeve 7 such that the fiber-optic cable will be at the bottom of the sleeve, as shown in FIG. 1. This positioning also facilitates replacement of the fiber-optic cable 29 when it is worn or otherwise in need of replacement. With the fiber optic cable lying along the bottom (with reference to FIG. 1) of the handpiece body 3, it is fairly easy to guide a replacement cable into the arch 55 of the manifold. If the cable were to lie along the side or top of the handpiece body (with reference to FIG. 1), gravity would pull the cable downwardly, making it more difficult to guide the cable into the arch 55 of the manifold 41.

Figures 9, 10:
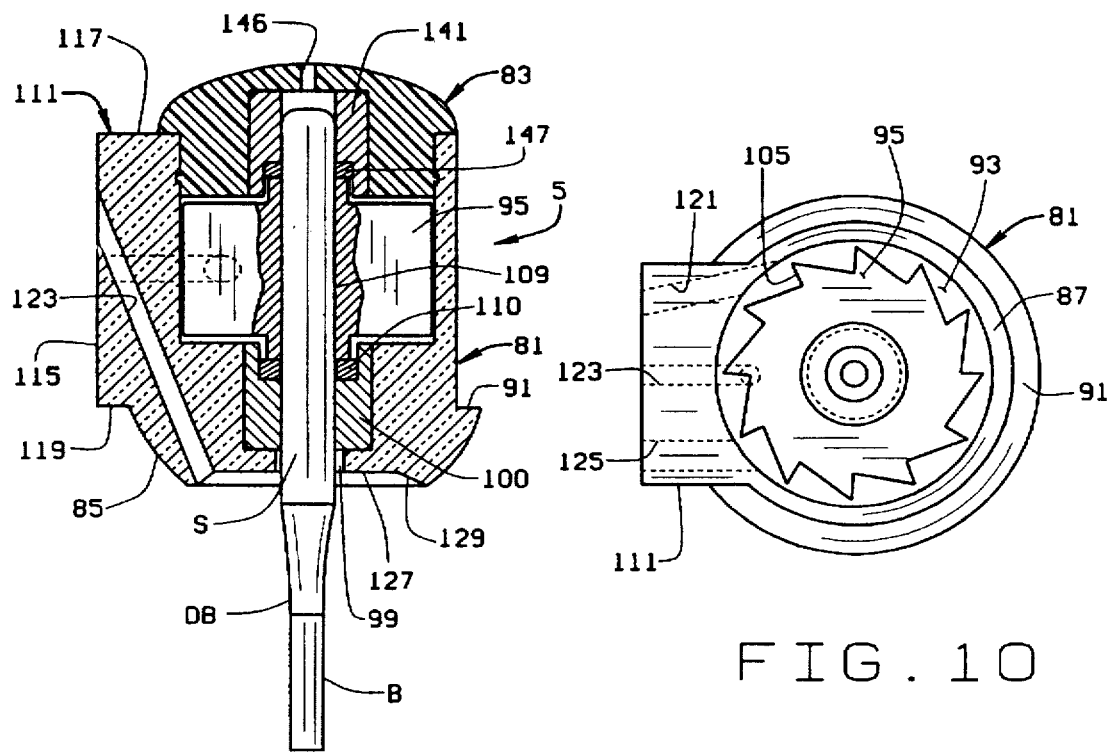
FIG. 9 is a cross-sectional view of the cartridge.
FIG. 10 is a top plan view of a body of the cartridge with a turbine placed in it.

A first illustrative embodiment of the disposable cartridge 5 is shown in FIGS. 7-13. The cartridge 5 is made of a hollow body 81 and a cap 83. The cartridge body 81 includes a base 85 and a circular wall 87 extending upwardly from the base. The wall 87 has an outer diameter sized to frictionally fit within the wall 61 of sleeve head 9. The top surface of the base 85 has a diameter equal to the outer diameter of the head wall 61 at its bottom surface 65. The wall 87 and base 85 thus form a shoulder 91. When the handpiece 1 is assembled, the cartridge shoulder 91 is adjacent the bottom surface 65 of head wall 61, as can be seen in FIG. 1. The cartridge wall 87 defines a generally cylindrical chamber 93 (FIG. 11) which receives a turbine 95. As best seen in FIGS. 9 and 11, the chamber 93 is counterbored as at 96. The counterbore 96 is coaxial with the inner surface of cartridge wall 87. The counterbore 96 does not extend completely through base 85 and has a floor 97. An opening 99 is formed in the center of the floor 97 to be concentric with the counterbore 96.

A bearing 100 is received in the counterbore 96. The bearing 100 includes a bearing body 101 defining, at the top thereof, a counter sunk area 102. A through bore 104 extends through the center of the bearing to be aligned with the opening 99 in the counterbore floor 97.

The turbine 95 (shown in FIGS. 10-12) has a turbine body 103 including a plurality of teeth 105. The teeth are oriented such that when air is blown across the teeth when the turbine is placed in the cartridge 5, the turbine 95 will rotate. The turbine 95 has upper and lower bosses 107 extending from the center of the upper and lower surfaces of the turbine. The bosses are axially aligned and a through bore 109 extends vertically through the center of the bosses 107. The bore 109 is sized to frictionally receive the shaft S of a drill bit DB. The lower boss 107 is received in the bearing counter sunk area 102 such that the turbine through bore 109 is axially aligned with the bearing through bore 104 and the opening 99. A washer 110 may be positioned in the bearing countersunk area 102 beneath the turbine boss 107 to facilitate positioning the turbine in the cartridge body chamber 93. Washer 110 may be a flat washer or a wave washer.

The cartridge body 81 also includes a heel 111 extending from the back of the body. The heel is generally rectangular in lateral cross-section and is sized and shaped to be received in the rectangular opening 67 in the body sleeve 7. The heel 111 is defined by generally straight or planar side walls 113, a back wall 115, an arcuate top surface 117, and an arcuate bottom surface 119. Three bores 121, 123, and 125 extend through the heel to place the cartridge chamber 93 in communication with the air supply bore 43, water supply bore 47, and the exhaust cut-out 57, respectively, in manifold 41. The heel 111 is preferably sized so that the back wall 115 of the heel 111 abuts the forward surface 51 of the manifold 41 when the handpiece is assembled. The heel acts as a key to align the bores and grooves of the manifold with the bores of the cartridge. This will ensure that the cartridge will be in the proper rotational position so that the openings into the cartridge for the operating air and water will be substantially aligned with their counterparts in the manifold 41. The heel could be replaced with a simple tennon to properly align the cartridge in the head, however, the heel provides the room needed to place the water tube in the cartridge so that the cooling water can be more appropriately directed, as is explained below.

The operating air bore 121 is generally circular and is in fluid communication with tube 27 and carries operating air into the cartridge body chamber 93. As best seen in FIG. 10, the bore 121 is not parallel to the longitudinal axis of the heel 111 or sleeve 7, but is rather at an angle to the axis to direct air at back surfaces or trailing edges of the turbine teeth 105 to rotate the turbine 95 in the cartridge 5. Bore 125 is in communication with manifold cut-out 57 to allow the operating air to be exhausted from cartridge 5. Preferably, the bore 125 is on a side of the heel opposite the air inlet bore 121. Bore 125 has a height preferably approximately equal to the height of the turbine 95 or its teeth 105. As seen in FIG. 8, bore 125 preferably has a straight, generally vertical edge 125a and an arcuate edge 125b. The arc of edge 125b is shaped to conform to the arc or curvature of the inner wall or surface of the sleeve 7 at the forward end of the sleeve, as seen in FIG. 5. Although the exhaust opening 125 is made of a straight and a curved edge, the opening could be made in any desired shape.

The water bore 123 extends diagonally through the heel 111 into the base 85 as seen in FIG. 9 and is in fluid communication with manifold bore 47 when the cartridge in placed in the body 3. Because bore 123 extends diagonally downwardly through the cartridge body 81, it forms an oval opening at the back wall 115 of the heel 111, as seen in FIG. 8. Bore 123 is placed in communication with tube 27 to deliver water through the cartridge body such that the water will exit the body at the bottom of the base 85, as seen in FIG. 9. The O-ring 53 and O-ring groove 49 formed in the front surface 51 of the manifold 41 are sized to surround the oval or oblong opening for bore 123 to create a substantially fluid tight seal between the cartridge 5 and manifold 41. The bottom of the cartridge body 81 has a countersunk area 127 surrounding the opening 99. The countersunk area is defined by a circular, radially inwardly flat, sloping wall or surface 129. Wall 129 is concentric about opening 99. The bore 123 opens into surface 129 and is angled and positioned such that water exiting bore 123 will be directed at a drill bit DB which is held by the turbine. Most existing high speed handpieces have a water exit in the sleeve. The positioning of the water outlet right at the drill bit, as is done here, further ensures that the water will actually contact the drill bit to cool the drill bit. Further, the water tube exit is in the disposable cartridge. Thus, the water tube exit, which will become contaminated during use, will be disposed of, making it easier to properly sterilize and clean the handpiece 1.

The cap 83 is generally circular in plan. It includes a top portion 131 and an annular wall 133 (FIG. 11). The wall 133 is sized to fit within wall 87 of the cartridge body 81 and forms a shoulder 135 with the top 131. The shoulder 135 sits on the top surface of cartridge wall 87 when the cartridge is assembled, as is seen in FIG. 9. The cap 83 has a bottom surface 137. The height of the wall 133 (from top to bottom) is sized so that the distance between the bottom surface 133 of cap 83 and the floor 97 of the cartridge body 81 will be slightly greater than the height of the turbine body 103 or the turbine teeth 105. A counterbore 139 is formed in the cap surface 133. A small diameter hole 146 is formed in the top of cap 83 concentrically to bore 139. Hole 146 allows for insertion of a tool to remove the drill bit DB from the cartridge, prior to disposal of the cartridge or to exchange the drill bit inserted in the cartridge with a different drill bit.

A second bearing 141 is received in the counterbore 139. Bearing 141 is substantially similar to the bearing 100 and includes a countersunk area 143 and a bore 145 formed in the center of the countersunk area. The turbine upper boss 107 is received in the second bearing counter sunk area 143 and a washer 147 may be positioned between the boss 107 and the bearing 141 in the countersunk area 143. Washer 147, like washer 110, may be a flat washer or a wave washer. The washers 110 and 147 axially or vertically position the turbine 95 in the cartridge 5 to minimize vertical movement of the turbine 95 relative to the cartridge 5 during use. This will eliminate vibrations which may otherwise be present and allow the handpiece to operate more smoothly. The washers provide a bearing between the turbine and bearing face. The washers are preferably made of a self lubricating material, such as OILITE®, an oil impregnated metal available from Beemer Precision, Inc. of Ft. Washington, Pa., or self-lubricating plastic, such as a phenolic resin available under the name IGUS T500 from Igus, Inc. of East Providence, R.I. A small amount of endplay may exist in the assembled cartridge. This endplay allows for free turning of the turbine.

The bearings are preferably inexpensive bushings made from a self-lubricating material such as a ceramic, a graphite, an oil impregnated metal (such as OILITE®), or a phenolic resin (such as IGUS T500). Other materials could also be used, including ball bearings. These bearings will ensure that the cartridge will operate smoothly for at least one session, yet are not so expensive as to make the cartridge too expensive to justify disposing of it after each use.

The cartridge body 81 and cap 83 are preferably made out of plastic, as is the turbine. The body 81 is preferably made from a translucent or clear plastic, such as LEXAN, to allow light from the fiber optic cable 29 to pass through the body 81. This will allow the dentist to illuminate the area in which he or she is working. The sloped wall 129 of the counterbore 127 facilitates directing the light towards the work area. The sloped wall 129 is directed toward the bit DB, as seen in FIG. 9, and directs, or focuses, light which passes into the cartridge body 81 toward the bit. Thus, the light will not be a diffuse light which merely passes out of the cartridge body 51, but will at least be partially directed toward the bit DB and the area in which the bit is being used. To further ensure that the light from the fiber optics is directed at the work area, the radial outer surfaces of the base can be dulled or coated with an opaque coating. Light will thus only be able to exit the cartridge at the bottom of the cartridge to light the work area from above. The light emitted from the cartridge will thus surround the drill bit. The dentist will thus have available light independent of the angle at which the handpiece is held. As can be appreciated, this handpiece assembly also brings the light much closer to the work area than do currently available high speed handpieces.

The light for the dentist is provided by the fiber-optic bundle 29 which extends through the handpiece sleeve 7 and abuts the back wall 115 of cartridge body heel 111. The fiber-optic bundle is operatively connected to a light source, as is known, to direct light to the cartridge 5. Because the cartridge body 81 is made of a transparent, or at least translucent, plastic, the body will be illuminated by the light emanating from the bundle 29. The light will exit the bottom of the cartridge body 81 to illuminate the area in which the dentist is using the drill. As can be appreciated, the cartridge body forms a part of the optics of the handpiece, in that the light passes through the handpiece. When the handpiece is used, the bottom surface of the cartridge may be etched by tooth material—that is the bottom surface effectively becomes sand blasted by tooth enamel. The same is true of conventional handpieces wherein the light is directed from the sleeve. However, when the procedure is complete, the cartridge is disposed of. Thus, the lens portion of the optics of the handpiece is also disposed of. When the cartridge is replaced with a new cartridge, a new lens (i.e. the cartridge body) is placed in the handpiece. This new lens will be clear of any blemishes and thus past drilling procedures will not effect the ability of the optic system of the handpiece to effectively light the work area.

The fiber optic bundle 29 can be permanently secured in the handpiece. However, it is preferably removable, as described above, so that it may be replaced if necessary. The fiber optic cable 29 is preferable a plastic fiber optic cable and can withstand both autoclaving and ultrasonic cleaning. However, if desired, the cable 29 can be removed after each use and prior to cleaning of the handpiece 7.

To assemble the cartridge 5, the first bearing 100 is seated in the counter bore 96 in the cartridge body 81. The first washer 110 is then seated in the bearing countersunk area 102 and the turbine 95 is then placed in the cartridge body 81 such that the operating air which enters the cartridge hollow 93 will be directed to the back of the turbine teeth 105 so that the turbine will be turned by the air forced into the cartridge. The second bearing 141 is placed in the cap 83 and the washer 147 is positioned in the bearing counter sunk area 143. The cap 83 is then inserted into the body 81. The cap is sized so that a friction fit is formed between the cap wall 133 and the cartridge body wall 87. The fit is snug enough that the cap cannot be easily removed from the body 81. The cartridge is supplied in its assembled form to the dentist. Therefore, the cap preferably is glued or ultrasonically welded to the body 81 to prevent the cartridge from being opened once it is assembled. The cap can also be provided with a annular detent 151 (FIG. 11) which is snappingly received in an annular groove 153 in the inner surface of the cartridge body wall 87. If the detent and groove are used, when the cartridge is snapped into place in the head of the body, the annular head will prevent the cartridge body from expanding, and the cap 83 will not be able to be removed from the cartridge body 81. The washers 110 and 147 are provided to minimize any vertical end play that the turbine may have in order to maintain the turbine vertically in a single position. A drill bit DB can then be inserted by the dentist into the cartridge 5. The drill bit is inserted into the bottom of the cartridge through the opening 99. It passes through the bearings and is frictionally received in the turbine bore 109 to be rotated with the turbine is rotated. The frictional grip of the turbine on the bit DB is sufficiently strong that the drill be can be operated at high speed, yet the drill bit may be removed from the cartridge to be changed if needed.

As is common, the drill bit DB has a bit portion B and a shaft portion S (FIG. 9). Unlike presently available high speed handpieces, the drill bit shaft S extends through bearing 100, turbine 95, and bearing 141. Further, unlike presently available handpieces, the turbine is not rotationally fixed in the bearings, rather it floats in the bearings. The drill bit shaft S thus acts as its own axis of rotation. If the turbine 95 were piloted in the bearings 100 and 141, extra eccentricities could be introduced into the rotation of the bit DB, depending on the alignment of the turbine bore 109 with the bores of the bearings. By piloting the drill bit shaft S in the bearings rather than the turbine, these eccentricities are avoided, enabling the bit to rotate more truly. This is true, even if the turbine is not quite centered with respect to the bearings.

Once the cartridge is assembled, the cartridge can be placed in the handpiece head. The cartridge is inserted in the head from the bottom of the head. It is simply pushed up into the area defined by the wall 61 until the shoulder 91 of the base 85 contacts the bottom 65 of the head wall 61, as seen in FIGS. 1 and 2. At that point, the bores 121, 123 and 125 will be aligned, and in fluid communication, with the bores 47, 43, and cut-out 47 of manifold 41. The handpiece is now ready to use. When the handpiece is used, the dentist will push down on the handpiece. The shoulder 91 will interfere with the wall 61 and the cartridge will not pass through the head. The cartridge is held in place in the head by a friction fit. The friction fit is sufficiently strong to hold the cartridge in place when the drill bit is pulled backwards across a tooth surface which is being worked upon. Yet the friction fit is not so strong that it cannot be overcome by a downward force on the cartridge so that the cartridge may be removed from the sleeve 7. When the drilling operation is complete, the cartridge is simply disposed of. All that remains to be cleaned is the handpiece body. As the handpiece has no bearings or other moving parts which can be harmed by an autoclave or an ultrasonic cleaning operation, the useful life of the handpiece will not be shortened and the handpiece body can be cleaned (ultrasonically) and sterilized via autoclave without harm to the body.

The cartridge 5 will preferably be provided to dentists in its assembled form. The dentist need only insert the cartridge in the handpiece and insert the drill bit DB into the cartridge.

A second embodiment of the cartridge 5' is shown in FIG. 14. Cartridge 5' is substantially similar to the cartridge 5. However, the bearings 100' and 141' are not cylindrical as are the bearings 100 and 141. Bearings 100' and 141' are rotatably or pivotally received in openings 96' and 139' so that they may rotate about an axis perpendicular to the vertical axis of the head 9 or drill bit DB. The openings 96' and 139' are not cylindrical as are the openings 96 and 139 of cartridge 5. Rather the walls of the openings 96' and 139' are arcuate, to allow the bearings to rotate about their vertical axes. The rotatability of the bearings 100' and 141' makes the bearings self-aligning. When the drill bit DB is inserted into the head, the bearings can rotate independently of each other so that the drill bit will pass through the bearing 100', turbine 95, bearing 141' and into bore 142'. Because the bearings can rotate relative to each other, their rotational position can be changed if necessary to assemble a smoothly running high speed handpiece. The alignment of the bearings in the cartridge 5' thus becomes less critical and more tolerance may be introduced into the manufacturing of the cartridge.

A third cartridge 205 is shown in FIGS. 15–17. The cartridge 205 includes a cartridge body 207 and a cartridge top or cap 209. The body 207 includes a base 211 and a generally cylindrical wall 213 which define a generally cylindrical chamber 215 which receives a turbine 217. As in cartridge body 81, the base 211 and wall 213 cooperate to define a shoulder 219 which serves as a stop, as explained above, when inserting the cartridge 205 into the handpiece body.

The turbine 217 includes a turbine body 221 which contains the teeth of the turbine, a boss 223 extending from a bottom of the turbine body, and a raised shoulder 225 formed on the top of the turbine body. The boss 223 and shoulder 225 each include a counter-sunk area 227, 229 which receives bearings 231 and 233. Washers 235 and 237 are received in the chamber 215 to preload the turbine to minimize axial movement of the turbine 217. The turbine has a bore 239 which extends through the body 221 and boss 223 and through which the drill bit's shaft S extends. As can be seen, the bore 239 has a sloped wall and narrows in diameter from top to bottom. At the bottom of the turbine, the bore 239 is substantially of the same diameter as the drill bit shaft S, and the turbine is press fit about the shaft S so that the drill bit DB will be driven by the rotating turbine. Splines extend radially inwardly from the sloped surface of the bore 239 to frictionally grip the drill bit shaft S.

As in cartridge body 81, the chamber 215 is stepped to define two counter-bores 241 and 243. The first counter-bore 231 is sized to receive turbine boss 223 such that the turbine may freely rotate in the chamber 215. The second, narrower counter-bore 233 is sized to accept washer 235. A through-bore 241 is formed in counter-bore 223 to allow for passage of the drill bit's shaft S into the cartridge to be removably received by the bearings 231, 233, the washers 235, 237, and the turbine 217.

The cartridge body 207 includes a heel 243 which has a back wall 245 which mates with the front 51 of the manifold 41. Openings 247, 249, and 251 for operating air, cooling water, and exhaust air, respectively, are formed in the back wall 245 of the heel. Unlike the heel 111 of cartridge body 81, the heel 243 is not substantially solid. The heel 243 includes an upper cutout 253 which opens into chamber 215. The cutout 253 is defined by generally vertical spaced apart side walls and a back wall 255. The back wall 255 is defined by a generally vertical surface 257 which extends downwardly from the top of the heel 243, a first sloped surface 259 which extends from the vertical surface, and a second sloped surface 261 which extends from the sloped surface 259 to the counter bore 241. The first sloped surface extends generally parallel to the cooling water tube 249. The second sloped surface 261 is not as steep as the first sloped surface 259, and forms an angle of between 30° and 40° to the vertical. The base also has a cut away section 263 which includes an upper sloped surface 265 and generally vertical side walls. The side walls of the cutouts 253 and 263 are co-planar, and the cutouts have the same width. As seen in FIG. 17, the cutouts are generally centered about the cooling water tube 249 and have a width equal to approximately 30% of the width of the heel 243. A narrow slot 267 extends to the shaft opening 241. Slot 267 is effectively in the same vertical plane (with reference to FIG. 15) as the water tube 249. The analogous slot 467 can be more clearly seen in FIGS. 28 and 29. The slot, which is narrower than the diameter of the burr tube shaft, creates an capillary type action, and has a tendency to draw some of the cooling water up into the lower bearing. This facilitates cooling and lubricating of the bearing. Some air exits through the opening 241, and a slight mist is also created around the shaft, and facilitates in cooling the shaft.

The cap 209 is substantially similar to the cap 83 of cartridge 81. The cap 209 includes a bore 271 into which the drill bit shaft S extends. Bore 251 is stepped, as at 273, to provide a shoulder which receives the washer 237. A bore 275, concentric with the bore 271, is formed in the top of the cap and allows for insertion of a tool to push the drill bit out of the cartridge. The cap 209 differs from the cap 83 in that it includes a heel 277 which closes the cutout 253 in the cartridge body heel 243. The cap heel 277 is defined by a top surface 279, a back surface 281, and a bottom surface 283. The back surface 281 is preferably beveled as at 285 to facilitate placement of the cap 209 onto the body 207.

The cartridge 205 is assembled and inserted in the handpiece body in substantially the same way as the cartridge 5. When the cartridge 205 is placed in the handpiece, the fiber optic bundle 29 will be opposite the sloped surfaces 259 and 261 of the cut out 253. The surfaces will act as mirrors, and light which enters the cartridge body will be reflected off these surfaces and pass out of the cartridge body through the surface 265 of cutout 263. The surfaces 259, 261, and 265 are formed such that they will reflect the light and aim it generally at the drill bit. This will provide direct lighting for the drill bit, in addition to the lighting around the work area. Stated differently, the cutouts will provide, in effect, a spot light effect which will provide an area of bright light at the drill bit, in addition to the wider spread of light provided by the clear cartridge body, as explained above in conjunction with the cartridge 5.

The cartridge 205' shown in FIG. 18 is substantially the same as the cartridge 205. However, rather than having the second cut out 263 in the base of the cartridge body, the cartridge body 207' includes added material 263' where the cut out 263 is formed in the cartridge body 207. The material 263' has a sloped surface 265' into which the cooling water tube 249 opens. Cartridge body 207' operates in the same way as the cartridge body 207. However, the effect is to move the surface 265' closer to the drill bit DB. The surfaces 265 and 265' are effectively the lenses of the cartridges 205 and 205' which create the spot light effect. Thus, the difference between the two is the placement of the lens.

A fourth embodiment of the cartridge is shown in FIG. 19. Internally, the cartridge 305 is substantially identical to the cartridge 205. The difference between the two cartridges 205 and 305 lies in the heel. The cartridge 305 includes a body 307 having a base 311 and a heel 343. A cutout 353 is formed in the base 311 and heel 343 of the cartridge body 307. The cutout includes side walls and a sloped upper wall 365. When the cartridge 307 is placed in the handpiece, the light which passes from the fiber optic bundle 29 will be directed at the surface 365 of cutout 353. The surface 365 will act as a mirror and reflect some of the light from fiber optic bundle through the cutout. The surface 365 is angled such that the light will be reflected toward the drill bit DB to provide a spot light effect at the work area. As with cartridges 205 and 5, the body is made of a transparent or translucent material, and light will also pass through the body and out of the base of the body to provide light around the drill bit as discussed above.

Two alternate embodiments for the turbine are shown in FIGS. 20–25. The turbine 401 of FIGS. 20–22 includes a turbine body 403 from which turbine blades 405 extend. The blades 405 are positioned near the top of the body 403. The body 403 has a height greater than that of the blades, and the bottom of the body 403 defines a boss 407 which is received in a bore in the body of the cartridge, as discussed above. A bore 409 extends through the body 403 to receive the shaft of the drill bit. The top and bottom surfaces of the turbine include circular recesses 411 surrounded by a circumferential wall 413. The recesses 411 and wall 413 are provided to accept bearings through which the drill bit shaft extends.

Figure 20:
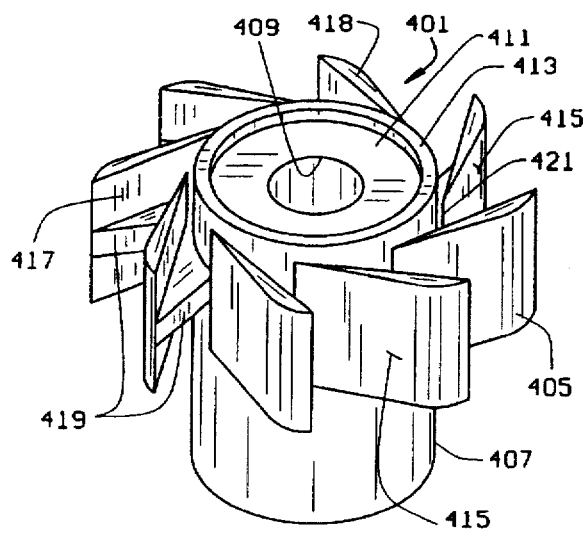
FIG. 20 is a perspective view of an alternative turbine for use with the handpiece.
Figure 21:
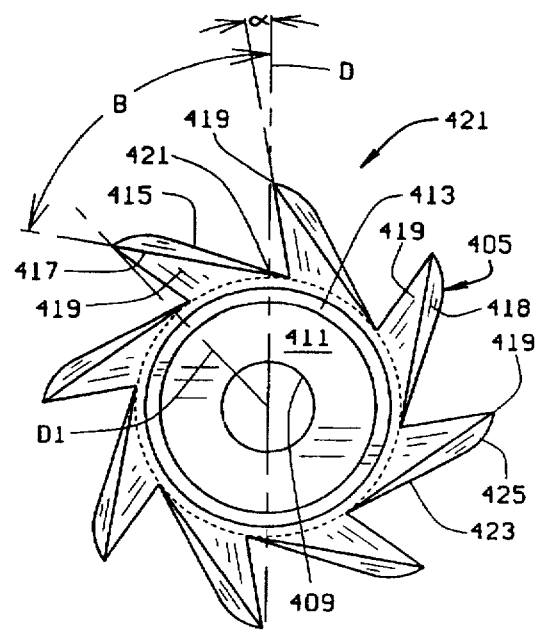
FIG. 21 is a top plan view of the turbine.
Figure 22:
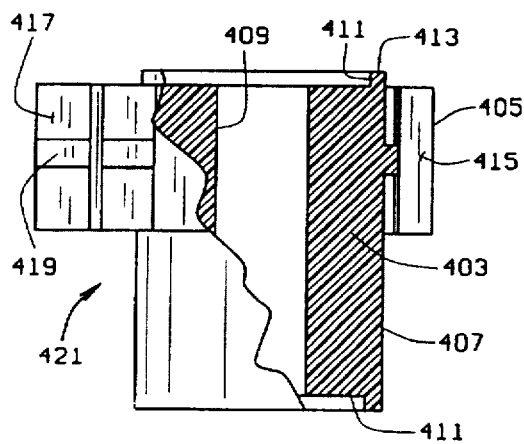
FIG. 22 is a side elevational view, partly in cross-section, of the turbine.

The turbine blades 405 are evenly spaced about the body 405 and extend tangentially from the turbine body 403. The blades 405 include a leading surface 415, a trailing surface 417, and generally planar top and bottom surfaces 418. The trailing surface is substantially planar and includes a buttress 419 which extends between the trailing surface and the outer surface of the turbine body. The buttress 419 is provided to connect the turbine blade 405 to the turbine body 403. As can be seen in FIG. 20, the blades 405 do not actually contact the body 403, and the forward edge 421 is slightly spaced from the body 403. The trailing surfaces 417 preferably form an angle α of about 12.5° with a diameter D which passes through the trailing edge 419 of the blade, and an angle β of about 80.7° with a diameter D1 which passes through the leading edge 421 of the blade. The trailing surface 417 of each blade extends from a point on the diameter D which passes through the trailing edge of a preceding blade to a diameter D1 which passes through the leading edge of a trailing blade, as best seen in FIG. 21.

The leading surfaces 415 of the blades 405 define an air foil. The air foil shape of the leading surfaces 415 is defined by a generally planar portion 423 and portion 425 which defines a segment or arc of a circle. The planar portion 423 is tangential to the arcuate portion 425, and the arcuate portion 425 leads into the trailing edge 419 of the blade. For a turbine having a blade diameter of about 0.3", the length of the trailing surface 417 is about 0.270", and the arcuate portion 425 is has a radius of about 0.045". Thus, the ratio of the length of the trailing surface 417 to the radius of the arcuate section 425 of the leading surface 415 is about 6.

When the cartridge is assembled with the turbine 401 and placed in the handpiece body, the operating air will blow against the trailing edge of the turbine blades 405 to cause the turbine 401 to rotate in the cartridge and to rotate the drill bit. The use of the air foil shaped blade will create a pressure differential between the leading and trailing surfaces. The pressure differential will enable the turbine to deliver greater torque to the drill bit.

Figure 23:
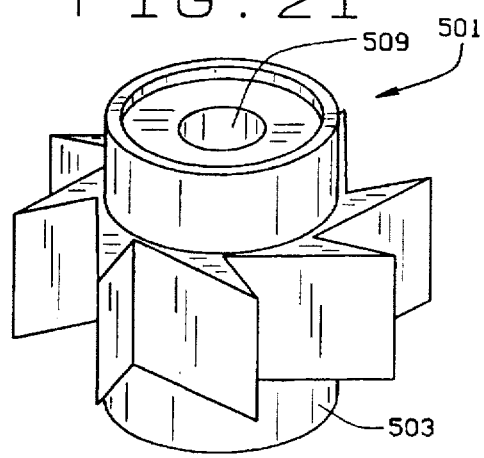
FIG. 23 is a perspective view of a third embodiment of the turbine.
Figure 24:
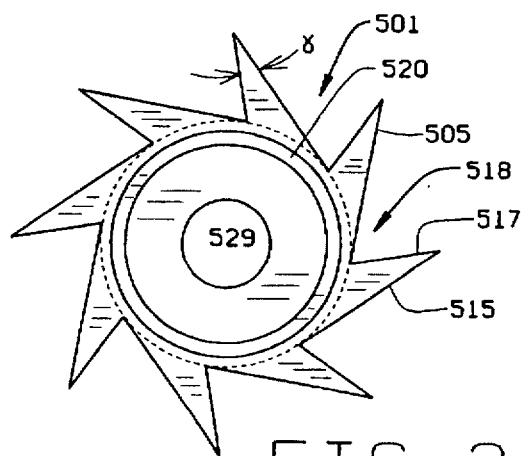
FIG. 24 is a top plan view of the turbine.
Figure 25:
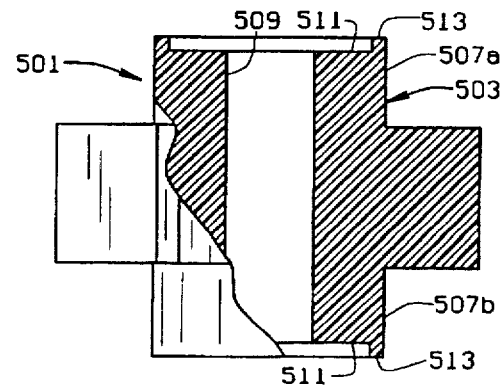
FIG. 25 is a side elevational view, partly in cross-section, of the turbine.
Figure 32:
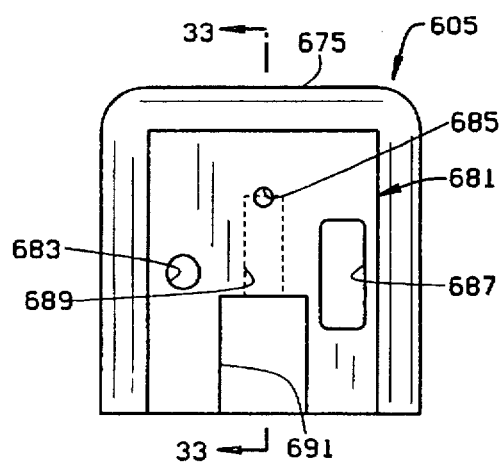
FIG. 32 is a rear elevational view of a top portion of the cartridge of FIG. 26
Figure 33:
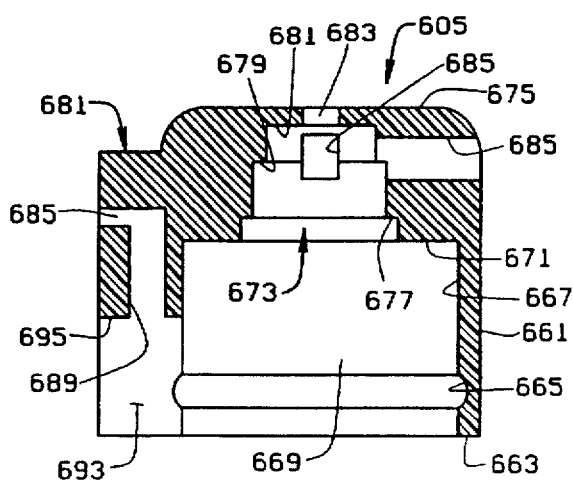
FIG. 33 is a cross-sectional view of the top portion taken along line 33—33 of FIG. 32.
Figure 34:
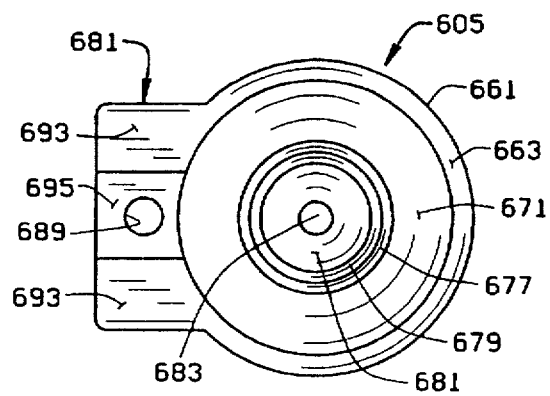
FIG. 34 is a bottom plan view of the top portion.
Figure 35:
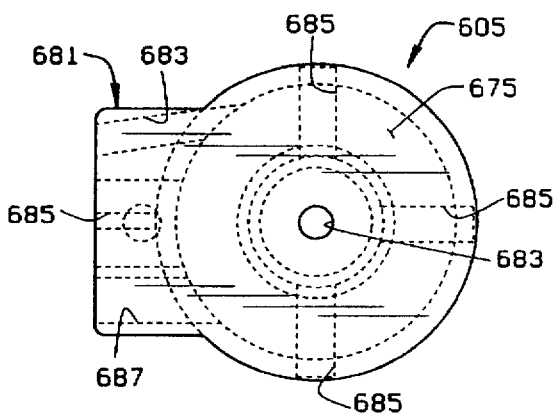
FIG. 35 is a top plan view of the top portion with the passages therein being shown in phantom.

The turbine 501 shown in FIGS. 23–25 is somewhat similar to the turbine 95 shown in FIG. 12. The turbine 501 includes a turbine body 503 with turbine blades 505 extending therefrom. The turbine blades 505 are centered generally along the length of the turbine body 503, and the body 503 defines upper and lower bosses 507a and 507b. A bore 509 extends through the body, and recesses 511 having circumferential walls 513 are formed in the outer surfaces of the bosses. The turbine blades 405 include a leading surface 515 and a trailing surface 517 and are generally triangular in shape. The difference between the blades of turbine 501 and turbine 95 is that the blades 505 of turbine 501 define a deeper throat 518 between the blades. Stated differently, the leading and trailing surfaces of the blades 505 are longer than the respective surfaces of blades 105 of turbine 95. The leading and trailing surfaces do not end at the body 503 of the turbine 501. Rather, there is a narrow annular base 520 from which the blades 505 extend. The leading and trailing surfaces of the blade 505 define an angle γ of about 23°. In a turbine having an overall diameter of about 0.3", the leading surface 515 and trailing surface 517 preferably have lengths of about 0.24" and 0.145", and the distance between the points where the leading and trailing surfaces join the base 520 is approximately 0.156". The triangle defined by the blade is formed by the angles about 23°, 27°, and 130°, where the intersection of the leading surface 515 with the base is about 27° and the intersection of the trailing surface with the base is about 130°. The ratio between the leading and trailing surfaces 15 and 517 is about 5:3.

When turbine 501 is used in an assembled handpiece, the operating air is blown against the trailing surface 517 of the blades 505. As can be appreciated, the trailing surface of blades 505 have a larger surface area than the trailing surfaces of blades 105 of the turbine 95. The design of the turbine blades 505 maximizes to a large degree the amount of surface area against which the operating air can be blown to rotate the turbine. This greater surface area will allow the turbine to deliver a greater power to the drill bit, than could be delivered with the turbine 95.

A fifth embodiment of the cartridge is shown in FIGS. 26–35. The cartridge 601 include a lower portion 603 and an upper portion 605 which, when connected, define a chamber 607 which houses a turbine 609.

The lower portion 603 is shown in detail in FIGS. 27–31. The lower portion 603 includes a base 611 having a generally convex lower surface 613. A generally circular wall 615 extends upwardly from the top of the base 611 and has a top surface 617. A semi-circular projection 619 extends outwardly from the wall 615 and circumscribes the wall 615. The outer diameter of the wall 615 is smaller than the diameter of the base 611 at its upper surface, and the base 611 and wall 615 define a shoulder 621. The portion of chamber 607 defined by the lower portion 603 is formed by a generally circular wall 623. The wall 623 is stepped, as at 625, to define a wall 627 of a smaller diameter. Wall 627 is stepped, as at 629, to define an opening 631 of a smaller diameter, and which extends through the base 611.

A heel 635 is extends from a back side of the bottom portion 603. The heel 635 is generally rectangular in rear elevation, as seen in FIGS. 27 and 28 and extends above the base 611. A lens portion 637 of the lower portion extends beneath the base and has sides co-linear with the sides of heel 635. The lens portion 637 gives the base the same appearance and shape as shown and described with respect to FIG. 18. The heel 637 includes a boss 639 which extends upwardly from the top surface 641 of the heel 635. The surface 641 is preferably generally planar and generally T-shaped, as seen in FIG. 29. A bore 643 is formed in the boss 639. The bore 643 includes a generally vertical section 645 (with reference to FIG. 31) and a sloped section 647. The section 647 of the bore 643 exits through the lower surface of the lens portion 635 of the cartridge lower portion 603. The section 647 is sloped or angled so that the exit is directed towards the bur DB, and preferably toward the bottom of the burr. The boss 639 has a generally vertical outer surface 649 which extends from the top of the boss to the top surface 641 of the heel 635. The heel 635 includes an inner surface 651 which slopes downwardly and inwardly from the top 641 of the heel to a generally horizontal surface 653. The boss 639 extends upwardly from a mount 654 having generally vertical side walls 655 and a sloped inner surface 656. The surface 656 is approximately as wide as the outer diameter of the boss 639. The surface 653 extends to the wall 623 which defines part of the chamber 607 of the cartridge 601.

The top portion 605 of the cartridge 601 is shown in more detail in FIGS. 32–35. The top portion 605 includes a generally annular wall 661 having a bottom surface 663 and a semicircular groove 665 formed on its inner surface 667. The inner surface 667 defines a downwardly opening chamber 669 having a top 671. A multi-stepped bore 673 extends through the top 671 of the chamber 669 to open through the upper surface 675 of the cartridge top portion 605. The bore 673 is stepped inwardly at 677, 679, and 681, each step defining a wall of smaller diameter, ultimately, to form the opening 683 which opens to the top surface 675 of the cartridge top portion 605. Three bores 685 extend radially and generally horizontally (with reference to FIGS. 33 and 35) from the two middle portions of the bore 673.

A heel 681, which is generally rectangular in rear elevation and top and bottom plan, extends from the back of the cartridge top portion 605. The heel 681 has three openings 683, 685, and 687 in its back surface which are operatively connected to operating air, cooling water, and exhaust paths, respectively, in the body of the handpiece. The opening 685 connects with a bore 689 which extends generally vertically (with reference to FIG. 33) through the heel 681. The heel includes a slot 691 defined by side walls 693 and a top surface 695. The slot 691 is generally centered with respect to the heel 681 and extends upwardly from the bottom surface 693 of the heel. The slot 691 opens into the chamber 669. The bore 689 opens into the slot top surface 695.

When the cartridge top portion 605 is placed on the cartridge bottom portion 603, the bottom surface 663 of the wall 661 of the top portion rests on the shoulder 621 of the bottom portion. The projection 619 of the bottom portion is received in the groove 665 of the top portion to snappingly lock the top and bottom portions together. The heels 635 and 681 of the top and bottom portions interlock or interengage with each other. The slot 691 of the top portion heel 681 is slightly greater in width than the heel 635 of the bottom portion and receives the bottom portion heel. The boss 639 of the bottom portion heel is received in the bore 689 of the top portion to place the tube 643 in fluid communication with the water supply. The top surface 695 of the slot 691 rests on the top surface 641 of the lower portion heel 635.

Prior to locking the top portion 605 to the bottom portion 603, the turbine 609 and bearings 701 must be placed in the cartridge portions. A bearing 701 is placed against step 629 in the cartridge lower portion and against step 679 in the cartridge upper portion. The steps 629 and 679 have a diameter slightly larger than the outer diameter of the bearings so that the bearings may freely spin in their respective areas. The turbine 609 is then positioned between the bearings. The turbine 609 includes spaced apart splines 610 which radiate inwardly from the inner surface of the turbine to frictionally grip the burr shaft. Thus, when the turbine is rotated by the operating air, the burr will rotate also. The turbine may be similar to the turbine such as shown in FIGS. 11 and 12.

Figure 36:
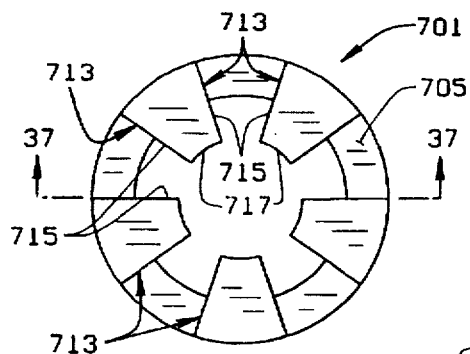
FIG. 36 is a plan view of an alternate bearing for use with the cartridge of FIG. 26.
Figure 37:
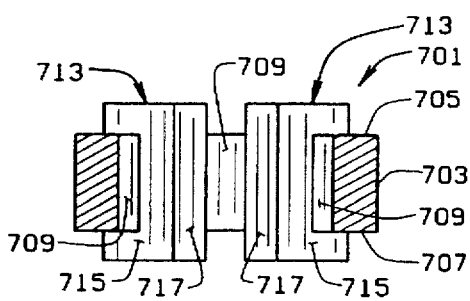
FIG. 37 is a cross-sectional view of the bearing taken along line 37—37 of FIG. 36.
Figure 38:
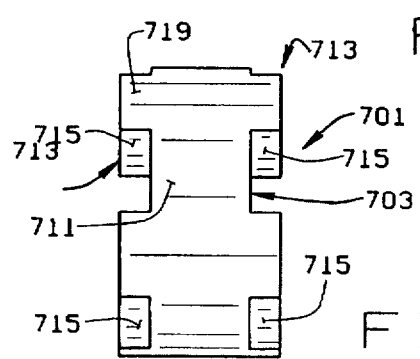
FIG. 38 is a side elevational view of the bearing of FIG. 36.

The bearings 701 are shown in detail in FIGS. 36–38. The bearings 701 include a ring 703 having upper and lower surfaces 705 and 707, an inner surface 709, and an outer surface 711. A plurality of evenly spaced apart bosses 713 radiate inwardly from the ring 703. The bosses extend above and below the ring 703, as seen in FIGS. 37 and 38, and include side walls 715, arcuate radially inner walls 717, and arcuate radially outer walls 719. The curvature of the outer walls 719 of the bosses 713 is equal to that of the ring 703. The curvature of the inner walls 717 of the bosses, and the extent to which the teeth extend into the ring 703, enable the surfaces or walls 717 of bosses 713 to act as bearing surfaces for the shaft S of the drill bit DB.

The bearings are made of a self-lubricating plastic, for example a phenol formaldehyde resin (commonly known as a phenolic resin) such as IGUS T500, sold by Igus, Inc. of East Providence, R.I. When the hand piece is run with such bearings, it has been noted that a ring of the bearing material forms around the shaft of the drill bit. Thus, some of the bearing material is adhering to the drill bit shaft. When the drill bit is operated, effectively the shaft does not contact the bearing, rather the bearing material which has rubbed off onto the shaft is contacting the bearing. Therefore, the bearing material is running or rubbing against itself. This produces a low friction environment which facilitates high speed operation of the turbine and helps to prevent undue heating of the handpiece and the drill bit. To facilitate this, the drill bit shaft is slightly rough in the vicinity of the bearing so that the bearing material will rub off onto the shaft.

The cartridge 601, when used with the bearing 701, allows for air cooling of the cartridge and the bur shaft B. When the cartridge 601 is placed in a handpiece, and operated, operating air will enter the chamber 607 through the passage 683, as described above. The operating air will, of course, contact the blades of the turbine to rotate the turbine. The construction of the bearings 701 create passage ways which allow the operating air to pass through the bearings and to the channels 685 in the upper portion 605. They also create an air passage way to allow air to exit the chamber through the opening 631 in the lower portion 603 of the cartridge. The air exiting the cartridge through the opening 631 will form a curtain of cool air around the bur DB, to facilitate cooling of the bur. Because the air exits the cartridge through the passages 685 in the upper portion 605 and the shaft hole 631 in the lower portion 603, the exhaust port 687 in the heel 681 can be eliminated, if desired. Further, the air exiting the cartridge 601 through the shaft opening 631 will entrain some of the water from tube 647. This will create a slight air/water mist around the drill bit shaft S to facilitate cooling of the shaft. If desired, some of the cooling water may be bled into the chamber 607. This bleed water would mix with the operating air to create a mist within the chamber which would facilitate cooling of the bearings and turbine to keep the cartridge cooler. It would also provide a lubricating effect to facilitate lubrication of the bearings.

As variations within the scope of the appended claims may be apparent to those skilled in the art, the foregoing description is set forth only for illustrative purposes and is not meant to be limiting. For example, the body could be made of plastic, rather than metal, and after a certain number of uses, the body could also be disposed of. O-rings could also be provided to make fluid tight seals between the cartridge and manifold for the air supply and air exhaust lines. The O-ring is autoclavable and is thus preferably mounted in the manifold. It could, however, be mounted in the cartridge. A detent and groove snap locking system could be provided on the outer surface of the cartridge and the inner surface of the handpiece head wall 61 to reinforce the frictional grip of the body head 9 on the cartridge 5. The manifold 41 could be integrally formed with the body 3 of the handpiece. The cartridge could be provided with a water bleed, to bleed water into the turbine chamber. This would further facilitate cooling and lubrication of the turbine and the bearings. Although a fiber optic bundle is disclosed to transmit light, the fiber optic bundle can be replaced with an optic tube or light tube which can transmit light between two points. These examples are merely illustrative.

I claim:

1. A high-speed dental/medical handpiece, the handpiece including:
   a body comprising a sleeve and a head at an end of said sleeve, said head having an opening; said sleeve carrying at least an air input tube, said air input tube being operatively connectable to a source of air, said body being made of an autoclavable material; and
   a cartridge removably received in said opening of said head of said body to removably receive a dental bit; said cartridge including a hollow cartridge body, a cap which closes said cartridge body, and a turbine; said cap and body cooperating to define a chamber which receives said turbine; said cartridge including an air input opening which is in communication with said air input line to provide operating air to drive said turbine and an exhaust outlet to exhaust said operating air from said chamber; said cartridge including a retainer to hold said cartridge in said body head during operation of said high-speed handpiece.

2. The handpiece of claim 1 wherein said body is made of metal and said cartridge is made of plastic and is disposable.

3. The handpiece of claim 1 wherein said sleeve carries an optic tube, said optic tube being operably connectable to a source of light and extending through said sleeve to provide light to a workarea in a patient's mouth where the bit is being used; said optic tube being removable from said handpiece.

4. The handpiece of claim 3 wherein said sleeve carries a water supply tube, said cartridge including a bore having an inlet in communication with said water supply tube and an outlet, said water supply tube being operably connectable to a source of water; said cartridge water bore being positioned to direct water to said bit.

5. The handpiece of claim 4 wherein said sleeve defines a forward end adjacent said handpiece body head, said handpiece body including a manifold received near said forward end of said sleeve; said manifold having:
   a first bore in fluid communication with said air supply tube and positioned to be in communication with said air inlet of said cartridge to place said cartridge chamber in communication with said air supply tube;
   a second bore in communication with said water supply tube and positioned to be in communication with said second bore in said cartridge to place said bore in communication with said water supply tube;
   a first longitudinally extending channel in communication with said exhaust outlet of said chamber; said sleeve defining an exhaust air flow path; and
   a second longitudinally extending channel which receives said optic tube.

6. The handpiece of claim 5 wherein said first and second channels in said manifold define grooves formed in an outer surface of said manifold.

7. The handpiece of claim 5 wherein said handpiece includes a connector at a back end thereof for connecting said handpiece to the sources of light, water, and air; said connector including a bore which receives said optic tube and a guide tube extending forwardly from said connector bore through at least a part of said sleeve, said optic tube slidingly extending through said connector bore and guide tube to be received in said manifold second opening, said optic tube being frictionally held in place by said guide tube.

8. The handpiece of claim 3 wherein said cartridge body is at least partially made of a material through which light can pass, said optic tube being in abutting contact with said cartridge body to deliver light into said cartridge body; said cartridge body having a bottom surface surrounding said bit, said light exiting from said cartridge body through said bottom surface and around said bit.

9. The handpiece of claim 8 wherein said cartridge body directs a portion of the light transmitted by the optic tube directly at the bit to provide a spot light at the bit; said cartridge body including a sloped surface positioned such that light from said optic tube is directed thereat, said sloped surface having an angle such that said sloped surface will reflect the light to the bit.

10. The handpiece of claim 8 wherein said cartridge includes a cut out in a bottom portion of the body, said sloped surface defining an upper surface of said cutout.

11. The handpiece of claim 8 wherein said cartridge includes a cut out in an upper portion of said body, said sloped surface defining at least a part of a rear wall of said cut out.

12. The handpiece of claim 1 wherein said turbine includes turbine blades, said turbine blades being substantially in the shape of an air foil.

13. The handpiece of claim 1 including an upper bearing and a lower bearing housed in said cartridge chamber; said turbine being positioned between said upper and lower bearings and having a bore; said upper and lower bearings each having a bore; said bores of said turbine and bearings being generally axially aligned with each other; said bore of said turbine being sized to frictionally receive said dental bit and said bores of said bearings being sized to rotatably receive said dental bit.

14. The handpiece of claim 13 wherein said turbine and bearing bores each have inner surfaces, said bore surfaces being in contact with said dental bit.

15. The handpiece of claim 13 wherein said bearings comprise bushings.

16. The handpiece of claim 15 wherein said bearings are made of a self-lubricating material.

17. The handpiece of claim 15 wherein the bearings are made from plastic.

18. The handpiece of claim 1 wherein the cartridge includes a shoulder near a bottom thereof, said cartridge shoulder being in abutting relationship with a bottom surface of said head of said handpiece body.

19. The handpiece of claim 18 wherein said cartridge is frictionally received in the head of the handpiece body.

20. The handpiece of claim 19 wherein said dental bit is frictionally held in said turbine.

21. The handpiece of claim 1 wherein said retainer comprises a shoulder formed at a bottom of said cartridge; said head of said handpiece body including a surface surrounding said handpiece body head opening, said shoulder abutting said surface of said handpiece body head.

22. A high-speed medical/dental handpiece, the handpiece including:

a body comprising a sleeve and a head at an end of said sleeve; said sleeve carrying at least an air input tube, said air input tube being operatively connectable to a source of air, said body being made of an autoclavable material; and a disposable cartridge removably received in said head of said body to removably receive a dental bit; said disposable cartridge including a hollow cartridge body, a cap which closes said cartridge body, and a turbine; said cap and body cooperating to define a chamber which receives said turbine; said cartridge including an air input opening which is in communication with said air input line to provide operating air to drive said turbine and an exhaust outlet to exhaust said operating air from said chamber; said cartridge body including a base and an wall extending upwardly from said base, said wall defining a surface of said chamber; said base having a diameter, at a widest part, greater than the outer diameter of said wall; said cartridge body wall having an outer diameter slightly smaller than an inner diameter of said head to be frictionally received in said head; said cartridge body base and said cartridge body wall defining a shoulder which abuts a bottom surface of said head.

23. The handpiece of claim 22 wherein said cap includes an upper portion and a cylindrical lower portion; said upper portion having a diameter greater than the diameter of said cylindrical lower portion, said upper portion and lower portions defining a shoulder which abuts a top surface of said wall of said cartridge body; said cylindrical lower portion being sized to be frictionally received within said cartridge body.

24. The handpiece of claim 23 wherein said cartridge cap is fixed to said cartridge body.

25. The handpiece of claim 23 wherein said cartridge cap and cartridge body are locked together; said cartridge cap including one of a rib and a groove on an outer surface of said lower portion, said cartridge body including the other of the detent and the groove on an inner surface of said cartridge body wall; said detent being received in said groove to snappingly lock said cap and body together.

26. The handpiece of claim 23 wherein said cartridge body base includes an upper surface defining a floor of said chamber; said floor defining a bore at the center thereof; said bore having a bottom surface defining a hole therethrough; said hole being positioned centrally of said bore; and said cap cylindrical lower portion defines a cartridge cap bore, said cartridge cap bore and said cartridge body bore being axially aligned; and said cartridge including bearings received in said bores; said turbine including an upper boss and a lower boss, said turbine bosses being received in said bearings.

27. The handpiece of claim 26 wherein said bearings are made of a self-lubricating material.

28. The handpiece of claim 26 wherein said cartridge includes washers positioned between said turbine and said bearings, said washers vertically positioning said turbine in said cartridge to substantially prevent axial movement of said turbine relative to said cartridge.

29. The handpiece of claim 26 wherein said turbine has a bore and said bearings have bores aligned with said turbine bore, said bit having a shaft which is extendible through said turbine bore and said bearing bores.

30. The handpiece of claim 29 wherein said turbine floats between said bearings; said bit shaft being rotatably receivable in said bearings and frictionally receivable in said turbine; said bit shaft defining its axis of rotation.

31. The handpiece of claim 29 wherein said bearings are self-aligning.

32. The handpiece of claim 31 wherein said cartridge body bore and said cap bore are defined by curved surfaces and said bearings having arcuate outer surfaces; said bearings being independently pivotal about a vertical axis in said bores, such that the bearing bores may be independently aligned with the turbine bore.

33. The handpiece of claim 26 wherein said bearings define air flow paths to facilitate cooling of said bearing and said bit.

34. The handpiece of claim 33 wherein a portion of said air exits said cartridge through said cartridge cap and a portion of said air exits said cartridge about a shaft of said bit, said cartridge cap including air outlets through which a portion of said air that passes though said bearings exit.

35. The handpiece of claim 33 wherein said bearings include a ring having an outer surface and an inner surface and a plurality of spaced apart radially inwardly extending bosses; said bosses extending above and below said ring and having an outer surface substantially flush with the outer surface of said ring and an inner surface spaced from the inner surface of said ring, the inner surface of said bosses being arcuate, said bosses being of a length sufficient to act as a bearing surface and locator for said bit, said bosses and said inner surface of said ring cooperating to define said air flow paths of said bearing.

36. A high-speed medical/dental handpiece, the handpiece including:

a body comprising a sleeve and a head at an end of said sleeve, said sleeve having a forward end adjacent said head; said sleeve carrying at least an air input tube, said air input tube being operatively connectable to a source of air, said body being made of an autoclavable material; and a disposable cartridge removably received in said head of said body to removably receive a dental bit; said disposable cartridge including a hollow cartridge body, a cap which closes said cartridge body, and a turbine; said cap and body cooperating to define a chamber which receives said turbine; said cartridge including an air input opening which is in communication with said air input line to provide operating air to drive said turbine and an exhaust outlet to exhaust said operating air from said chamber;

a optic tube in said sleeve, said optic tube being operably connectable to a source of light and extending through said sleeve to provide light to a workarea in a patient's mouth where the bit is being used; said optic tube being removable from said handpiece;

a water supply tube in said sleeve, said cartridge including a bore having an inlet in communication with said water supply tube and an outlet, said water supply tube being operably connectable to a source of water; said cartridge water bore being positioned to direct water to said bit;

a manifold received near said forward end of said sleeve; said manifold having a first bore in fluid communication with said air supply tube and positioned to be in communication with said air inlet of said cartridge to place said cartridge chamber in communication with said air supply tube; a second bore in communication with said water supply tube and positioned to be in communication with said bore in said cartridge to place said bore in communication with said water supply tube; a first longitudinally extending channel in communication with said exhaust outlet of said chamber; said sleeve defining an exhaust air flow path; and a second longitudinally extending channel which receives said optic tube;

a cutout at said forward end of said sleeve, said cutout being defined by side walls and opening into said handpiece body head; said manifold having a forward surface flush with said forward end of said sleeve; said cartridge including a heel which is received in said cutout; said heel having a back surface substantially adjacent said forward surface of said manifold such that cartridge air inlet, exhaust outlet, and water bore are in fluid communication with said manifold first bore, first opening, and second bore, respectively.

37. The handpiece of claim 36 wherein said cartridge water bore extends, at least in part, diagonally downwardly toward a bottom surface of said cartridge.

38. The handpiece of claim 37 wherein said cartridge bottom surface includes a recess defined by an annular sloped surface, said water bore outlet being at said sloped surface.

39. The handpiece of claim 36 wherein said heel includes a sloped surface against which at least a part of the light from said optic tube is directed, said sloped surface reflecting light directly at the bit.

40. A cartridge adapted to be removably received in ahead of a body of a high-speed handpiece of a medical/dental instrument and to receive a bit; said cartridge including:

a cartridge body having a base, a wall extending upwardly from said base, and a hole formed centrally of said base through which a dental bit can pass, said base and wall defining an upwardly opening chamber, said chamber having a floor;

a cap mounted to the cartridge body to close the chamber;

a turbine received in said cartridge body chamber, said turbine including a turbine body having plurality of blades and a bore extending axially through said turbine; and upper and lower bearings received in said chamber; said turbine being positioned between said bearings to float between said bearings in said cartridge when the bit is not received in the cartridge.

41. The cartridge of claim 40 wherein said cap includes an upper portion and a cylindrical lower portion; said upper portion having a diameter greater than the diameter of said cylindrical lower portion, said cap upper portion and cap lower portion defining a shoulder which abuts said wall of said cartridge body; said cylindrical lower portion diameter being sized to be frictionally received within said cartridge body; said lower portion being sized such that the distance between said cap lower portion and said chamber floor is slightly greater than the height of said turbine blades.

42. The cartridge of claim 41 including a cartridge body bore formed in said chamber floor and a cartridge cap bore formed in said cap cylindrical lower portion; said cartridge cap bore and said cartridge body bore being axially aligned; said turbine including at least one of an upper boss and a lower boss which is at least partially received in a respective one of said upper and lower bearings.

43. The cartridge of claim 42 wherein said turbine includes two bosses, said bearings being received in said cap and body bores, said bearings defining bores which receive said turbine bosses.

44. The cartridge of claim 41 wherein said turbine defines recesses in upper and lower surfaces thereof, said bearings being received in said recesses of said turbine.

45. The cartridge of claim 42 including washers associated with upper and lower surfaces of said turbine to vertically position said turbine in said cartridge to substantially prevent axial movement of said turbine relative to said cartridge.

46. The cartridge of claim 42 wherein said bearings have bores aligned with said turbine bore.

47. The cartridge of claim 46 wherein said bearings are self-aligning.

48. The cartridge of claim 47 wherein said cartridge body bore and said cap bore are defined by curved surfaces and said bearings have arcuate outer surfaces; said bearings being independently pivotal about a vertical axis in said bores, such that the bearing bores may be independently aligned with the turbine bore.

49. The cartridge of claim 40 wherein said cartridge body includes a heel; said heel including an air input bore and a water supply bore; said air input bore communicating with said enclosure to supply operating air to said turbine; said cartridge including an air exhaust bore to exhaust operating air from said enclosure; said water bore being formed to direct water to said bit.

50. The cartridge of claim 49 wherein said cartridge body base includes a bottom surface, said bottom surface defining a counterbored area, said counterbored area being defined by a sloped wall; said water bore having an exit in said sloped wall.

51. The cartridge of claim 49 wherein at least said cartridge body is made from a light transmitting plastic to form a portion of an optic system.

52. The cartridge of claim 51 wherein said cartridge body includes a sloped surface against which light is directed by a light source, said sloped surface directing at least some of said light from said light source directly to a work area to provide a spot light effect at said work area.

53. The cartridge of claim 52 wherein said cartridge body includes a slot formed at least partially in said heel, said sloped surface defining a surface of said slot; said slot extending from a top of said cartridge body, said sloped surface defining at least in part, a bottom of said slot.

54. The cartridge of claim 53 including a second slot co-linear with said first slot and which extends upwardly from said base of said cartridge body, said second slot having a sloped upper surface.

55. The cartridge of claim 52 wherein said cartridge body includes a slot formed at least partially in said heel, said sloped surface defining a surface of said slot; said slot extending upwardly from a bottom of said cartridge body, said sloped surface defining a top of said slot.

56. A high-speed dental/medical handpice, the handpiece including:

a body comprising a sleeve and a head at an end of said sleeve; said head defining a chamber; said sleeve carrying an air input tube connectable to a source of air to deliver air to said chamber, a water supply tube connectable to a source of water, and an optic tube connectable to a source of light; and a turbine and independently received in said chamber; wherein said optic tube is removably and independently received in said handpiece to facilitate replacement of said optic tube within said sleeve.

57. The handpiece of claim 56 wherein said handpiece includes a connector at a back end thereof for connecting said handpiece to said sources of light, water, and air; said connector including a bore which slidingly receives said optic tube and a guide tube extending forwardly from said connector bore through at least a part of said sleeve, said optic tube slidingly extending through said connector bore and said guide tube.

58. The handpiece of claim 56 wherein a portion of said head is made of light transmitting material, said optic tube extending though said sleeve to abut said portion of said head, said portion of said head being formed to direct light toward a workarea.

59. The handpiece of claim 58 wherein said head of said handpiece includes said head of said body and a disposable cartridge; said disposable cartridge being removably and frictionally received in said body head; said cartridge including a cartridge body; said light transmitting portion of said head comprising said cartridge body.

60. A method of assembling a high-speed medical/dental handpiece, said handpiece including an autoclavable body, a disposable cartridge, and a dental bit removably receivable in said cartridge; said handpiece body having a sleeve, a head formed at an end of said sleeve, an air supply line, and a water supply line extending though said sleeve to be in fluid communication with said body head; said cartridge defining an enclosure, said cartridge including an upper bearing, a lower bearing, a turbine received in said enclosure between said bearings, an air supply bore in communication with said enclosure, an air exhaust in communication with said enclosure, and a water supply bore formed to direct water toward said bit; said method including removably inserting said cartridge in said head of said handpiece body such that said air supply line is in communication with said air supply bore and said water supply line is in fluid communication with said water supply bore, inserting said dental bit in said cartridge, and passing a shaft of said dental bit through said lower bearing, through said turbine, and at least partially into said upper bearing.

61. In a high speed medical/dental handpiece including:
a body comprising a sleeve and a head at an end of said sleeve; said head defining a chamber, a turbine rotatably received in said chamber, an opening in a bottom of said head to allow for a dental bit to be inserted into said chamber, an air supply tube extending through said sleeve and being connectable to a source of air to deliver air to said chamber to rotatably drive said turbine, a water supply tube extending through said sleeve and being operably connectable to a supply of water to direct water towards the bit driven by said turbine, and an optic system for delivering light to a workarea; the improvement comprising:
said optic system, said optic system delivering said light from said head bottom surface, the light delivered from said head bottom surface surrounding said opening in said head bottom surface.

62. The improvement of claim 61 wherein at least a portion of said head is made of light transmitting material; said optic system including an optic tube extending through said sleeve and being in abutting relationship with said light transmitting portion of said head, said bottom surface of said head being made of said light transmitting material.

63. The improvement of claim 62 wherein said water supply tube defines at least a part of a water supply path, said head having a bottom surface, said water supply path having an exit in said head bottom surface; said bottom surface including a countersunk area defined by a sloping annular wall concentric with said bit; said water path exit being formed in said annular wall to direct said water at said bit.

64. The improvement of claim 62 wherein said at least a portion of said head made from light transmitting material includes a sloped surface against which at least a part of the light from said optic tube is directed, said sloped surface reflecting light directly at the bit.

65. The improvement of claim 64 wherein said at least a portion of said head includes a slot, said sloped surface defining a surface of said slot.

66. The improvement of claim 65 wherein said slot extends upwardly from a bottom of said head, said sloped surface defining an upper surface of said slot.

67. The improvement of claim 61 wherein said head includes a pair of bearings; the improvement further including said turbine floating between said bearings; said bearings and said turbine receiving a shaft of a bit such that the bit shaft defines an axis of rotation for said turbine and said bit.

68. The improvement of claim 61 wherein said turbine includes a turbine body and turbine blades extending from said body, said turbine blades defining an airfoil and including a leading surface and a generally planar trailing surface.

69. The improvement of claim 68 wherein said leading surface of said turbine blade includes a generally planar section and an arcuate section, said arcuate section being defined by a radius, wherein the ratio of the length of said trailing surface to said radius is about 6.

70. The improvement of claim 68 wherein said turbine blade is spaced from said turbine body, said turbine including a buttress which connects said turbine blade to said turbine body.

71. The improvement of claim 61 wherein said head includes a pair of bearings between which said turbine is positioned, aid bearings defining air flow paths to facilitate cooling of said bearing and said bit.

72. The improvement of claim 71 wherein a portion of said air exits said cartridge through said cartridge cap and a portion of said air exits said cartridge about a shaft of said bit, said cartridge cap including air outlets through which a portion of said air that passes though said bearings exit.

73. The improvement of claim 71 wherein said bearings include a ring having an outer surface and an inner surface and a plurality of spaced apart radially inwardly extending bosses; said bosses extending above and below said ring and having an outer surface substantially flush with the outer surface of said ring and an inner surface spaced from the inner surface of said ring, the inner surface of said bosses being arcuate, said bosses being of a length sufficient to locate a shaft of said bit, said bosses and said inner surface of said ring cooperating to define said air flow paths of said bearing.

74. A high-speed medical/dental handpiece including a body comprising a sleeve and a head at an end of said sleeve; said head defining a chamber having a floor, a turbine rotatably received in said chamber, an opening in said chamber floor to allow for a bit to be inserted into said chamber, upper and lower bearings in said chamber; and a turbine received in said chamber; said bit having a shaft, said bit shaft being passed through said lower bearing, said turbine, and at least partially into said upper bearing; said bit shaft rotatably supporting said turbine between said bearings.

75. The handpiece of claim 74 wherein said turbine floats axially and/or laterally in said chamber when said bit shaft is not received in said chamber.

76. The handpiece of claim 74 wherein said bit shaft defines an axis of rotation for said bit and for said turbine.

77. A high speed dental/medical handpiece including a body comprising a sleeve and a head at an end of said sleeve; said head receiving a bit; said head including an optic system, said optic system including a prism on a lower surface of said head to focus light towards said bit.

78. The handpiece of claim 77 wherein a bottom portion of said handpiece head is made of a light transmitting material, said prism being formed in said light transmitting portion of said handpiece.

79. The handpiece of claim 78 wherein said handpiece includes a disposable cartridge, said cartridge comprising a portion of said handpiece head; said disposable cartridge including said light transmitting material.

80. A high-speed medical/dental handpiece operable at speeds in excess of 50,000 rpm, said handpiece including a body comprising a sleeve and a head at an end of said sleeve; said head defining a chamber having a floor, a turbine rotatably received in said chamber, an upper bearing above said turbine and a lower bearing below said turbine, said upper and lower bearings being plastic sleeve bearings.

81. The high-speed handpiece of claim 80 wherein the plastic sleeve bearings are made from a high-heat plastic.

82. The high-speed handpiece of claim 81 wherein the plastic sleeve bearings are made from a self-lubricating plastic.

83. The high-speed handpiece of claim 81 wherein the plastic sleeve bearings are made from a phenolic resin.

* * * * *